US010765706B2

(12) United States Patent
Borlongan et al.

(10) Patent No.: US 10,765,706 B2
(45) Date of Patent: Sep. 8, 2020

(54) METHOD OF STEM CELL DELIVERY INTO THE BRAIN DURING CHRONIC DISEASE USING BLOOD BRAIN BARRIER PERMEABILIZERS

(71) Applicants: Cesario Venturina Borlongan, Tampa, FL (US); Paul R. Sanberg, Spring Hill, FL (US)

(72) Inventors: Cesario Venturina Borlongan, Tampa, FL (US); Paul R. Sanberg, Spring Hill, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/257,315

(22) Filed: Sep. 6, 2016

(65) Prior Publication Data
US 2017/0065643 A1 Mar. 9, 2017

Related U.S. Application Data

(60) Provisional application No. 62/214,027, filed on Sep. 3, 2015.

(51) Int. Cl.
*A61K 35/51* (2015.01)
*A61K 47/26* (2006.01)
*A61K 9/00* (2006.01)

(52) U.S. Cl.
CPC ............ *A61K 35/51* (2013.01); *A61K 9/0019* (2013.01); *A61K 47/26* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 6,627,405 B1 | 9/2003 | Nandabalan et al. |
| 7,674,457 B2 | 3/2010 | Borlongan et al. |
| 2001/0038836 A1 | 11/2001 | During et al. |
| 2002/0028510 A1 | 3/2002 | Sanberg et al. |
| 2004/0197310 A1 | 10/2004 | Sanberg et al. |
| 2005/0169902 A1 | 8/2005 | Borlongan et al. |
| 2006/0159666 A1 | 7/2006 | Willing et al. |

FOREIGN PATENT DOCUMENTS

| | | |
|---|---|---|
| EP | 1658853 A1 | 5/2006 |
| WO | 2005/059115 A1 | 6/2005 |

OTHER PUBLICATIONS

Misra et al., Stem cell therapy in ischemic stroke: Role of IV and intra-arterial therapy, Neurology 2012; 79; S207-S212.*
Hou et al., Induction of umbilical cord blood mesenchymal stem cells into neuron-like cells in vitro, Int J Hematol., Oct. 2003; 78(3): 256-61.*
Andreollo et al., ABCD Arq. Bras Cir Dig, 2012; 25(1), pp. 49-51 (Year: 2012).*
Briggs et al., British Journal of Hospital Medicine, vol. 77, No. 5, published online May 11, 2016, p. C66 (Year: 2016).*
Borlongan et al., Future Neurol. Aug. 2015; 10(4): 313-319 (Year: 2015).*
Gonzales-Portillo et al., Cell Transplant. 2014: 23 (0): 531-539, published online Jan. 29, 2014 (Year: 2014).*
Guo et al., Stem Cell Research & Therapy, 2013; 4:116 (Year: 2013).*
Lindvall et al., Stroke, 2011; 42: 2369-2375 (Year: 2011).*
Shen et al., Journal of Cerebral Blood Flow & Metabolism (2007) 27, 6-13 (Year: 2007).*
Bicknese, et al., Human umbilical cord blood cells can be induced to express markers for neurons and glia. Cell Transplant. 2002;11(3):261-264.

(Continued)

*Primary Examiner* — Scott Long
*Assistant Examiner* — Evelyn Y Pyla
(74) *Attorney, Agent, or Firm* — Michele L. Lawson; Robert J. Varkonyi; Smith & Hopen, P.A.

(57) ABSTRACT

Blood brain barrier (BBB) permeabilizers, such as mannitol, can facilitate the entry of stem cells from the periphery to the stroke brain. It is unknown whether BBB permeation in the chronic stage of the disease still facilitates the entry of stem cells from the periphery to the injured brain. Evidence herein shows BBB permeation in the chronic stage of stroke assisted in the entry of stem cells from the periphery to the stroke brain. Stroke models treated with human umbilical cord stem cells (hUCBC) only (2 million viable cells), mannitol or a combination. Results revealed that hUCBC alone or combined with mannitol displayed significant behavioral and histological deficits compared to control animals, with the HUCBC-mannitol combined treatment showing improvements over hUCBC only treatments in brain cell survival in the peri-infarct area. BBB permeation in chronic stroke also lowers the effective stem cell dose necessary to improve functional outcomes.

9 Claims, 15 Drawing Sheets

(56) References Cited

OTHER PUBLICATIONS

Borlongan, et al., Transplantation of cryopreserved human embryonal carcinoma-derived neurons (NT2N Cells) promotes functional recovery in ischemic rats. Exp Neurol. Feb. 1998;149(2): 310-321.
Borlongan, et al., Viability and survival of hNT neurons determine degree of functional recovery in grafted ischemic rats. Neuroreport. Aug. 24, 1998;9(12):2837-2842.
Borlongan, et al., Cerebral ischemia and Cns transplantation: differential effects of grafted fetal rat striatal cells and human neurons derived from a clonal cell line. Neuroreport. Nov. 16, 1998;9(16):3703-3709.
Broxmeyer, et al., Commentary: a rapid proliferation assay for unknown co-stimulating factors in cord blood plasma possibly involved in enhancement of in vitro expansion and replating capacity of human hematopoietic stem/progenitor cells. Blood Cells. 1994;20(2-3):492-497.
Chen, et al., Intravenous administration of human umbilical cord blood reduces behavioral deficits after stroke in rats. Stroke, Nov. 2001;32(11):2682-2688.
Chiang, et al., Transplantation of fetal kidney tissue reduces cerebral infarction induced by middle cerebral artery ligation. J Cereb Blood Flow Metab. Dec. 1999;19(12):1329-1335.
Johnston, et al., Trophic factor secreting kidney cell lines: in vitro characterization and functional effects following transplantation in ischemic rats. Brain Res. May 11, 2001;900(2):268-276.
Kim, et al., Ex vivo expansion of human umbilical cord blood-derived T-lymphocytes with homologous cord blood plasma. Tohoku J. Exp. Med. Feb. 2005;205(2):115-122.
Lam, et al., Preclinical ex vivo expansion of cord blood hematopoietic stem and progenitor cells: duration of culture; the media, serum supplements, and growth factors used; and engraftment in NOD/SCID mice. Transfusion. Dec. 2001;41(12):1567-1576.
Lu, et al., Intravenous administration of human umbilical cord blood reduces neurological deficit in the rat after traumatic brain injury. Cell Transplant. 2002;11(3):275-281.
Mayani, & Lansdorp, Biology of human umbilical cord blood-derived hematopoietic stem/progenitor cells. Stem Cells. 1998;16(3):153-165.
Nishino & Borlongan, Restoration of function by neural transplantation in the ischemic brain. Prog Brain Res. 2000;127:461-476.
Nishino, et al., Striatal grafts in the ischemic straitum improve pallidal GABA release and passive avoidance. Brain Res Bull. 1993;32(5):517-520.
Roof, et al., A comparison of long-term functional outcome after 2 middle cerebral artery occlusion models in rats. Stroke. Nov. 2001;32(11):2648-57.
Sanchez-Ramos, et al., Expression of neural markers in human umbilical cord blood. Exp Neurol. Sep. 2001;171(1):109-115.
Saporta, et al., Human umbilical cord blood stem cells infusion in spinal cord injury: engraftment and beneficial influence on behavior. J. Hematother Stem Cell Res. Jun. 2003;12(3):271-278.
Todaro, et al., Haematopoietic progenitors from umbilical cord blood. Blood Purif. 2000;18(2):144-147.
Vajpayee, et al., Evaluation of umbilical cord serum therapy for persistent corneal epithelial defects. Br. J. Ophthalmol. Nov. 2003;87(11):1312-1316.
Yoon, et al., Application of umbilical cord serum eyedrops for the treatment of neurotrophic keratitis. Ophthalmology. Sep. 2007;114(9):1637-1642.
Examiner's First Report issued by the Australian Government on Dec. 18, 2008 for related Australian Patent Application No. 2004247071.
International Search Report and Written Opinion issued by the International Searching Authority dated May 11, 2005 for related International Patent Application No. PCT/US2004/042043.
Restriction Requirement issued by the United States Patent and Trademark Office dated Feb. 13, 2007 for related U.S. Appl. No. 11/012,849.
Non-Final Office Action issued by the United States Patent and Trademark Office dated May 4, 2007 for related U.S. Appl. No. 11/012,849.
Final Office Action issued by the United States Patent and Trademark Office dated Nov. 8, 2007 for related U.S. Appl. No. 11/012,849.
Non-Final Office Action issued by the United States Patent and Trademark Office dated Apr. 30, 2008 for related U.S. Appl. No. 11/012,849.
Non-Final Office Action issued by the United States Patent and Trademark Office dated Nov. 10, 2008 for related U.S. Appl. No. 11/012,849.
Final Office Action issued by the United States Patent and Trademark Office dated May 6, 2009 for related U.S. Appl. No. 11/012,849.
Non-Final Office Action issued by the United States Patent and Trademark Office dated Sep. 14, 2011 for related U.S. Appl. No. 12/719,565.
Non-Final Office Action issued by the United States Patent and Trademark Office dated Jun. 27, 2012 for related U.S. Appl. No. 12/719,565.
Final Office Action issued by the United States Patent and Trademark Office dated Nov. 29, 2012 for related U.S. Appl. No. 12/719,565.
Non-Final Office Action issued by the United States Patent and Trademark Office dated Apr. 1, 2014 for related U.S. Appl. No. 12/719,565.
Communication pursuant to Article 94(3) EPC (EPO Form 2001) issued by the European Patent Office dated Jun. 16, 2008 for related European Patent Application No. 04814249.1.
Robinson, P.J. and S. I. Rapoport. Size selectivity of blood-brain barrier permeability at various times after osmotic opening. Am J Physiol Sep; 253(3 Pt 2): R459-466.
Stock Solutions, Equipment, and Laboratory Guidelines. Common Stock Solutions, Buffers, and Media, Current Protocols in Neuroscience, 2001. 00:2A:A.2A.1-A.2A.8.
Stem Cells: Scientific Progress and Future Research Directions. Report prepared by the National Institutes of Health, Jun. 2001.
Toxicological Evaluation of Some Antimicrobials, Antioxidants, Emulsifiers, Stabilizers, Flour-Treatment Agents, Acids and Bases. FAO Nutrition Meetings, Report Series No. 40A, B, C. Who/Food Add./67.29.
Alemdar, A.Y., et al. Tenth Annual Conference of the American Society for Neural Transplantation & Repair. Experimental Neurology 181 (2003) 84-112.
Armstrong, Beth K., et al. Size-Dependent Blood-Brain Barrier Opening Demonstrated with [14C]Sucrose and a 200,000-Da [3H]Dextran. Experimental Neurology 97, 686-696 (1987).
Amar, Arun Paul, et al. Endovascular Restorative Neurosurgery: A Novel Concept for Molecular and Cellular Therapy of the Nervous System. Neurology 52:402-413, 2003.
Angstrom from Wikipedia. Accessed on Feb. 13, 2012.
Bath, Philip MW, and Nikola Sprigg. Colony stimulating factors (including erythropoietin, granulocyte colony stimulating factor and analogues) for stroke. Cochrane Database Syst Rev Apr. 18, 2007;(2):CD005207.
Bernardo, Allitia B., et al. The Clinical Potential of Minocycline in Amyotrophic Lateral Sclerosis. US Neurological Disease 2006—May 2006.
Blau, Helen et al. Something in the Eye of the Beholder, Science, 2002, vol. 298, No. 5592, pp. 361-363.
Aihara, Noritaka, et al. Striatal Grafts in Infarct Striatopallidum Increase Release, Reorganize GABAa, Receptor and Improve Water-maze Learning in the Rat. Brain Research Bulletin, vol. 33, No. 5, pp. 483-488, 1994.3.
Albers, Gregory W., et al. Intravenous Tissue-Type Plasminogen Activator for Treatment of Acute Stroke: The Standard Treatment with Alteplase to Reverse Stroke (STARS) Study. The Journal of the American Medical Association, vol. 283(9), 1 Mar. 2000, pp. 114-1150.
Altumbabica, Mensura and Marc R. Del Bigio. Transplantation of the fetal brain tissue into the site of intracerebral hemmorage in rats. Neuroscience Letters 257 (1998) 61-64.
Broxymeyer, H.E Questions to be answered regarding umbilical cord blood hematopoietic stem and progenitor cells and their use in transfusion. Transfusion, vol. 35, No. 8, 1995.
Broxmeyer, Hal E., et al. High-Efficiency Recovery of Functional Hematopoietic Progenitor and Stem Cells from Human Cord Blood

(56) References Cited

OTHER PUBLICATIONS

Cryopreserved for 15 Years. Proceedings of the National Academy of Sciences of the United States of America, vol. 100, No. 2 (Jan. 21, 2003), pp. 645-650.

Broxmeyer, Hal E., et al. Growth characteristics and expansion of human umbilical cord blood and estimation of its potential for transplantation in adults. Proc. Natl. Acad. Sci. USA, vol. 89, pp. 4109-4113. May 1992.

Borlongan, Cesario V. et al. Bradykinin receptor agonist facilitates low-dose Cyclosporine-A protection against 6-hydroxydopamine neurotoxicity. Brain Research, vol. 956, Issue 2, Nov. 29, 2002, pp. 211-220.

Hess, D.C. and C.V. Borlongan. Stem cells and neurological diseases. Cell Prolif. 2008, 41 (Suppl. 1), 000-000.

Borlongan, Cesar V. et al. Central Nervous System Entry of Peripherally Injected Umbilical Cord Blood Cells Is Not Required for Neuroprotection in Stroke. Stroke, 35(10):2385-2389.

Lu, Li et al. Stem cells from bone marrow, umbilical cord blood and peripheral blood for clinical application: current status and future application. Critical Reviews in Oncology/Hematology 22 (1996) 61-78.

Borlongan, Cesario V. et al. Cerebral ischemia and CNS transplantation: differential effects of grafted fetal rat striatal cells and human neurons derived from a clonal cell line. NeuroReport 9, 3703-3709 (1998).

Borlongan, Cesario V. et al. Cyclosporine-A enhances choline acetyltransferase immunoreactivity in the septal region of adult rats. Neuroscience Letters 279 (2000) 73-76.

Borlongan, Cesario V. et al. Cyclosporine A-Induced Hyperactivity in Rats: Is it Mediated by Immunosuppression, Neurotrophism, or Both? Cell Transplantation, vol. 8, pp. 153-159, 1999.

Borlongan Cesario V. And Paul R. Sanberg. Elevated Body Swing Test: A New Behavioral Parameter for Rats with 6- Hydroxydopamine-Induced Hemiparkinsonism. The Journal of Neuroscience, Jul. 1995, 15(7): 5372-5378.

Borlongan, C.V. and D.F. Emerich. Facilitation of drug entry into the CNS via transient permeation of blood brain barrier: laboratory and preliminary clinical evidence from bradykinin receptor agonist, Cereport. Brain Research Bulletin 60 (2003) 297-306.

Borlongan, C.V. et al. Involvement of Gdnf in Neuronal Protection against 6-OHDA-Induced Parkinsonism Following Intracerebral Transplantation of Fetal Kidney Tissues in Adult Rats. Neurobiology of Disease 8, 636-646 (2001).

Borlongan, Cesario V. et al. Locomotor and Passive Avoidance Deficits Following Occlusion of the Middle Cerebral Artery. Physiology & Behavior, vol. 58, No. 5, pp. 909-917, 1995.

Borlongan, C.V. et al. Melatonin-Secreting Pineal Gland: A Novel Tissue Source for Neural Transplantation Therapy in Stroke. Cell Transplantation, vol. 12, pp. 225-234, 2003.

Borlongan, Cesario V. et al. Neural transplantation for neurodegenerative disorders. Surgery, vol. 353, Apr. 1999.

Borlongan, Cesario V. et al. Striatal Dopamine-Mediated Motor Behavior Is Altered Following Occlusion of the Middle Cerebral Artery. Pharmacology Biochemistry and Behavior, vol. 52, No. 1, pp. 225-229, 1995.

Borlongan, Cesario V. et al. Transplantation of Cryopreserved Human Embryonal Carcinoma-Derived Neurons (NT2N Cells) Promotes Functional Recovery in Ischmic Rats. Experimental Neurology 149, 310-321 (1998). Article No. EN976730.

Borlongan, C.V. et al. Upregulation of CNS Trophic Factors by Human Umbilical Cord Transplants is Essential for Veuroprotection Against Acute Stroke. Program No. 789.17. 2003 Abstract Viewer/Itinery Planner. Washington, DC: Society for Neuroscience, 2003. Online.

Borlongan, Cesario V. et al. Viability and survival of hNT neurons determine degree of functional recovery in grafted schemic rats. NeuroReport 9, 2837-2842 (1998).

Brines, Michael L. et al. Erythropoietin Crosses the Blood-Brain Barrier to Protect against Experimental Brain Injury. Proceedings of the National Academy of Sciences of the United States of America, vol. 97, No. 19 (Sep. 12, 2000), pp. 10526-10531.

Castro, Raymond F. et al. Failure of Bone Marrow Cells to Transdifferentiate into Neural Cells in Vivo. Science, vol. 297 (Aug. 23, 2002).

RMP 7 Compound Summary, PubChem Public Chemical Database, http://pubchem.ncbi.nlm.nih.gov/summary/summary.cgi?cid=64145 &loc=ec_rcs, accessed on Nov. 15, 2011.

Chang, Chen-Fu et al. Intravenous Administration of Bone Morphogenetic Protein-7 After lschemia Improves Motor Function in Stroke Rats. Stroke, 2003, vol. 34, pp. 558-564.

Chang, C.F. et al. Hyperbaric Oxygen Therapy for Treatment of Postischemic Stroke in Adult Rats. Experimental Neurology 166, 298-306 (2000).

Chiang, Yung-Hsiao et al. Transplantation of Fetal Kidney Tissue Reduces Cerebral Infarction Induced by Middle Cerebral Artery Ligation. Journal of Cerebral Blood Flow & Metabolism (1999) 19, 1329-1335.

Cornford, Eain M. and Marcia E. Corford. New systems for delivery of drugs to the brain in neurological disease. The Lancet. Neurology vol. 1, Sep. 2002, pp. 306-315.

DiGiusto, David L. et al. Hematopoietic Potential of Cryopreserved and Ex Vivo Manipulated Umbilical Cord Blood Progenitor Cells Evaluated in Vitro and in Vivo. Blood, 87:1261-1271, 1996.

Dillon-Carter, Ora et al. T155g-Immortalized Kidney Cells Produce Growth Factors and Reduce Sequelae of Cerebral Ischemia. Cell Transplantation, vol. 11, pp. 251-259, 2002.

Doggrell, Sheila A. A neuroprotective derivative of erythropoietin that is not erythropoietic. Expert Opin. Investig. Drugs (2004) 13(11):1517-1519.

Dunnett, Stephen B. et al. Cell therapy in Parkinson's disease—stop or go? Nature Reviews. Neuroscience, vol. 2 (May 2001), pp. 365-369.

Ehrenreich, Hannelore et al. Erythropoietin Therapy for Acute Stroke Is Both Safe and Beneficial. Molecular Medicine 8(8): 495-505, 2002.

Emerich, Dwaine F. and Shelley R. Winn. Immunoisolation Cell Therapy for CNS Diseases. Critical Reviews in Therapeutic Drug Carrier Systems, 18(3):265-298 (2001).

Emerich, Dwaine F. and Heather C. Salzberg. Update on Immunoisolation Cell Therapy for CNS Diseases. Cell Transplantation, vol. 10, pp. 3-24, 2001.

Emerich, Dwaine F. Use of the Bradykinin Agonist, Cereport as a Pharmacological Means of Increasing Drug Delivery to the CNS. Curr. Med. Chem.—Imun., Endoc. & Metab. Agents, 2002, 2, 109-123.

Evenson, Kelly R. et al. Prehospital and In-Hospital Delays in Acute Stroke Care. Neuroepidemiology 2001;20:65-76.

Folkerth, Rebecca D. Abnormalities of Developing White Matter in Lysosomal Storage Diseases. Journal of Neuropathology and Experimental Neurology, vol. 58, No. 9, Sep. 1999, pp. 887-902.

Gluckman, Eliane et al. Outcome of Cord-Blood Transplantation from Related and Unrelated Donors. The New England Journal of Medicine, Issue: vol. 337(6), Aug. 7, 1997, pp. 373-381.

Guidott, J.E. et al. Retrovirus-mediated enzymatic correction of Tay-Sachs defect in transduced and non-transduced cells. Human Molecular Genetics, 1998, vol. 7, No. 5, pp. 831-838.

Harvey, B.K. et al. HSV amplicon delivery of glial cell line-derived neurotrophic factor is neuroprotective against schemic injury. Experimental Neurology 183 (2003) 47-55.

Hatanaka, Masakazu. Sugar Effects on Murine Sarcoma Virus Transformation. Proc. Nat. Acad. Sci. USA, vol. 70, No. 5, pp. 1364-1367, May 1973.

Hill, James H. et al. Iron-Induced Enhancement of 67Ga Uptake in a Model Human Leukocyte Culture System. Journal of Nuclear Medicine, vol. 16, No. 12, pp. 1183-1186.

Johnston, Rowena E. et al. Trophic factor secreting kidney cell lines: in vitro characterization and functional effects following transplantation in ischemic rats. Brain Research 900 (2001) 268-276.

(56) References Cited

OTHER PUBLICATIONS

Katzan, Irene L. et al. Use of Tissue-Type Plasminogen Activator for Acute Ischemic Stroke: The Cleveland Area Experience. The Journal of the American Medical Association, Issue: vol. 283(9), Mar. 1, 2000, pp. 1151-1158.
Kawada, Hiroshi et al. Administration of Hematopoietic Cytokines in the Subacute Phase After Cerebral Infarction Is Effective for Functional Recovery Facilitating Proliferation of Intrinsic Neural Stem/Progenitor Cells and Transition of Bone Marrow-Derived Neuronal Cells. Journal of the American Heart Association, Circulation 2006:113:701-710.
Kipnis, Jonathan and Michal Schwartz. Dual action of glatiramer acetate (Cop-1) in the treatment of CNS autoimmune and neurodegenerative disorders. TRENDS in Molecular Medicine, vol. 8, No. 7, Jul. 2002, pp. 319-323.
Kordower, Jeffrey H. et al. Neurodegeneration Prevented by Lentiviral Vector Delivery of GDNF in Primate Models of Parkinson's Disease. Science, vol. 290, Oct. 27, 2000. pp. 767-773.
Tenth Annual Conference of the American Society for Neural Transplantation & Repair, Experimental Neurology, 2003, vol. 181, pp. 84-112.
Kreek, Mary Jeanne et al. Pharmacotherapy of Addictions. Nature Reviews, Sep. 2002, vol. 1, pp. 710-726.
Lindvall, Olle et al. Grafts of Fetal Dopamine Neurons Survive and Improve Motor Function in Parkinson's Disease. Science, vol. 247. pp. 574-577.
Ling, Zao Dung et al. Partial purification of pramipexole-induced trophic activity directed at dopamine neurons in ventral mesencephalic cultures. Brain Research 791 (1998) 137-145.
Lundberg, Cecilia et al. Differentiation of the RN33B Cell Line into Forebrain Projection Neurons after Transplantation into the Neonatal Rat Brain. Experimental Neurology 175, 370-387 (2002).
Zigova, Tanja et al. Human Umbilical Cord Blood Cells Express Neural Antigens After Transplantation Into the Developing Rat Brain. Cell Transplantation, vol. 11, pp. 265-274, 2002.
Donner, O. Machala L. et al. A Full Expression of the Genome of Rous Sarcoma Virus in Heterokaryons Formed after Fusion of Virogenic Mammalian Cells and Chicken Fibroblasts. J. gen. Virol. (1970), 8, 219-229.
Makinen, Susanna et al. Human umbilical cord blood cells do not improve sensorimotor or cognitive outcome following transient middle cerebral artery occlusion in rates. Brain Research 1123 (2006) 207-215.
Mezey, Eva et al. Transplanted bone marrow generates new neurons in human brains. Proceedings of the National Academy of Sciences of the United States of America, vol. 100, No. 3 (Feb. 4, 2003), pp. 1364-1369.
Mezey, Eva et al. Comment on Failure of Bone Marrow Cells to Transdifferentiate into Neural Cells in Vivo. Science 299, 1184b (2003).
Newcomb, Jennifer D. et al. Timing of Cord Blood Treatment After Experimental Stroke Determines Therapeutic Efficacy. Cell Transplantation, vol. 15, pp. 213-223, 2006.
Nishino, Hitoo and Cesario V. Borlongan. Restoration of function by neural transplantation in the ischemic brain. Progress in Brain Research, 2000, vol. 127, pp. 461-476.
Nishino, H. et al. Striatal Grafts in the Ischemic Striatum Improve Pallidal Gaba Release and Passive Avoidance. Brain Research Bulletin, vol. 32, pp. 517-520, 1993.
Ikragly Angela J. and Mary Haak-Frendscho. An Acid-Treatment Method for the Enhanced Detection of GDNF in Biological Samples. Experimental Neurology 145, 592-596 (1997).
Pardridge, William M. Drug and Gene Delivery to the Brain: The Vascular Route. Neuron, vol. 36, 555-558, Nov. 14, 2002.
NINDS Parkinson's Disease Information Page, http://www.ninds.nih.gov/disorders/parkinsons_disease/parkinsons_disease.htm. Accessed on Feb. 13, 2012.
What is Parkinson's Disease (PD)? National Parkinson Foundation, http://www.parkinson.org/Parkinson-s-Disease/PD-101/What-is-Parkinson-s-Disease. Accessed on Dec. 12, 2011.
Parkinson's Disease. The New York Times Health Guide, http://health.nytimes.com/health/guides/disease/parkinsons-disease/overview.html. Accessed on Dec. 12, 2011.The Neuroscientist, vol. 8, No. 5, 2002. pp. 457-488.
Redmond, Jr., D. Eugene. Cellular Replacement Therapy for Parkinson's Disease—Where We Are Today?
Salmon, Patrick et al. High-level transgene expression in human hematopoietic progenitors and differentiated blood lineages after transduction with improved lentiviral vectors. Blood, vol. 96, No. 10, Nov. 15, 2000. pp. 3592-3598.
Sanberg, Paul R. et al. Testis-derived Sertoli cells have a trophic effect on dopamine neurons and alleviate hemiparkinsonism in rats. Nature Medicine, vol. 3, No. 10, Oct. 1997. pp. 1129-1132.
Sawa, Akira and Solomon H. Snyder. Schizophrenia: Neural Mechanisms for Novel Therapies. Molecular Medicine, Jan./Feb. 2003; pp. 3-9.
Schleffier, Bjorn et al. Marrow-mindedness: a perspective on neuropoiesis. Trends Neurosci. (1999) 22, 348-357.
Schneider, Armin et al. The hematopoietic factor G-CSF is a neuronal ligand that counteracts programmed cell death and drives neurogenesis. The Journal of Clinical Investigation, vol. 115, No. 8, Aug. 2005. pp. 2083-2098.
Shyu, Woei-Chemg et al. Functional Recovery of Stroke Rats Induced by Granulocyte Colony-Stimulating Factor-Stimulated Stem Cells. Journal of the American Heart Association. Circulation, 2004, vol. 110, pp. 1847-1854.
Steiner, Thorsten, et al. Treatment options for large hemispheric stroke. Neurology, 2001, vol. 57, No. 2, pp. S61-S68.
Taguchi, Akihiko et al. Administration of CD34+ cells after stroke enhances neurogenesis via angiogenesis in a mouse model. The Journal of Clinical Investigation, vol. 114, No. 3, Aug. 2004, pp. 330-338.
Testoni, Nicoleta et al. A New Method of "In-Cell Reverse Transcriptase-Polymerase Chain Reaction" for the Detection of BCR/ABL Transcript in Chronic Myeloid Leukemia Patients. Blood, vol. 87, No. 9 (May 1, 1996), pp. 3822-3827.
Theise, Neil D. et al. Comment on "Little Evidence for Developmental Plasticity of Adult Hematopoietic Stem Cells." Science 299, 1317a (2003).
Tsuboi, Atsushi and Renato Baserga. Effect of 5-Bromo-2-deoxyuridine on Transport of Deoxyglucose and Cycloleucine in 3T6 Fibroblasts. Cancer Research 33, 1326-1330, Jun. 1973.
Van Bree, J.B.M.M. et al. Drug transport across blood-brain barrier. I. Anatomical and physiological aspects. Pharm Weekbl [Sci] 1992;14(5):305-310.
Vendrame, Martina et al. Infusion of Human Umbilical Cord Blood Cells in a Rat Model of Stroke Dose-Dependently Rescues Behavioral Deficits and Reduces Infarct Volume. Stroke, 35(10):2390-2395.
Volkmar, Fred R. and David Pauls. Autism. The Lancet, vol. 362, Oct. 4, 2003. pp. 1133-1141.
Ratajczak, Mariusz et al. Very Small Embryonic Like (VSEL) Stem Cells—Characterization, Development Origin and Biological Significance. Exp Hematol. Jun. 2008; 36(6): 742-451.
Wagers, Amy J. et al. Little Evidence for Developmental Plasticity of Adult Hematopoietic Stem Cells. Science, New Series, vol. 297. No. 5590 (Sep. 27, 2002), pp. 2256-2259.
Wagner, John E et al. Transplantation of Umbilical Cord Blood After Myeloablative Therapy: Analysis of Engraftment. Blood, vol. 79, No. 7 (Apr. 1, 1992): pp. 1874-1881.
Wang, Yun et al. Glial Cell Line-Derived Neurotrophic Factor Protects against Ischemia-Induced Injury in the Cerebral Cortex. The Journal of Neuroscience, Jun. 1, 1997, 17(11):4341-4348.
Wang, Yun et al. Methamphetamine Potentiates Ischemia/Reperfusion Insults After Transient Middle Cerebral Artery Ligation. Journal of the American Heart Association. Stroke, 2001, vol. 32, pp. 775-782.
Wang, Lei et al. Treatment of Stroke with Erythropoietin Enhances Neurogenesis and Angiogenesis and Improves Neurological Function in Rats. Journal of the American Heart Association. Stroke, 2004, vol. 35, pp. 1732-1737.

(56) References Cited

OTHER PUBLICATIONS

Weimann, James M. et al. Contribution of transplanted bone marrow cells to Purkinje neurons in human adult brains. PNAS, Feb. 18, 2003, vol. 100, No. 4, pp. 2088-2093.

Willing, A.E. et al. Intravenous Versus Intrastriatal Cord Blood Administration in a Rodent Model of Stroke. Journal of Neuroscience Research 73:296-307 (2003).

Heo, Jun. Seok et al. Comparison of molecular profiles of human mesenchymal stem cells derived from bone marrow, umbilical cord blood, placenta and adipose tissue. International Journal of Molecular Medicine. 37: 115-125, 2016.

Bang, Oh Young et al. Autologous Mesenchymal Stem Cell Transplantation in Stroke Patients. American Neurological Associated, 2005. Annals of Neurology, vol. 57, No. 6, pp. 874-882.

Lee, Jin Soo et al. A Long-Term Follow-Up Study of Intravenous Autologous Mesenchymal Stem Cell Transplantation in Patients With Ischemic Stroke. Stem Cells 2010;28:1099-1106. www.StemCells.com.

Rocco, Andrea et al. Monitoring After the Acute Stage of Stroke. A Prospective Study. Stroke, Apr. 2007, vol. 38, No. 4: 1225-1228. Available at http://www.strokeaha.org. DOI: 10.1161/01.STR.0000259659.91505.40.

Borlongan, et al. Cell-based therapy in ischemic stroke. NIH Public Access Author Manuscript. Expert Rev Neurother. Aug. 2008; 8(8): 1193-1201. doi:10.1586/14737175.8.8.1193.

Borlongan, et al. Central Nervous System Entry of Peripherally Injected Umbilical Cord Blood Cells Is Not Required for Neuroprotection in Stroke. Stroke, Oct. 2004: 2385-2389. doi: 10.1161/01.STR.0000141680.49960.d7.

Cui, et al. Top 3 Behavioral Tests in Cell Therapy Studies After Stroke. Stroke, Nov. 2017: 3165-3167. doi: 10.1161/STROKEAHA.117.018950.

Hess and Borlongan. Stem cells and neurological diseases. Cell Prolif. 2008, 41 (Suppl. 1), 94-114.

Yoo, et al. Enhanced Recovery From Chronic Ischemic Injury by Bone Marrow Cells in a Rat Model of Ischemic Stroke. Cell Transplantation, 2015. vol. 24, pp. 167-182.

\* cited by examiner

METHOD OF STEM CELL DELIVERY INTO THE BRAIN DURING CHRONIC DISEASE USING BLOOD BRAIN BARRIER PERMEABILIZERS

REFERENCE TO RELATED APPLICATIONS

This application claims priority to U.S. Provisional Patent Application Ser. No. 62/214,027, entitled "Method of Stem Cell Delivery into the Brain During Chronic Disease using Blood Brain Barrier Permeabilizers", filed Sep. 3, 2015, the contents of which are hereby incorporated by reference into this disclosure.

FIELD OF INVENTION

This invention relates to treating chromic neuronal diseases. Specifically, the invention addresses treating chronic neurodegenerative diseases, using stem cells and blood brain barrier permeabilizers.

BACKGROUND OF THE INVENTION

Stroke treatment consists of two categories: prevention and acute management. Prevention treatments currently consist of antiplatelet agents, anticoagulation agents, surgical therapy, angioplasty, lifestyle adjustments, and medical adjustments. An antiplatelet agent commonly used is aspirin. The use of anticoagulation agents seems to have no statistical significance. Surgical therapy appears to be effective for specific sub-groups. Angioplasty is still an experimental procedure with insufficient data for analysis. Lifestyle adjustments include quitting smoking, regular exercise, regulation of eating, limiting sodium intake, and moderating alcohol consumption. Medical adjustments include medications to lower blood pressure, lowering cholesterol, controlling diabetes, and controlling circulation problems.

Acute management treatments consist of the use of thrombolytics, neuroprotective agents, Oxygenated Fluorocarbon Nutrient Emulsion (OFNE) Therapy, Neuroperfusion, GPIIb/IIIa Platelet Inhibitor Therapy, and Rehabilitation/Physical Therapy.

A thrombolytic agent induces or moderates thrombolysis, and the most commonly used agent is tissue plasminogen activator (t-PA). Recombinant t-PA (rt-PA) helps reestablish cerebral circulation by dissolving (lysing) the clots that obstruct blood flow. It is an effective treatment, with an extremely short therapeutic window; it must be administered within 3 hours from onset. It also requires a CT scan prior to administration of the treatment, further reducing the amount of time available. Genetech Pharmaceuticals manufactures ACTIVASE® and is currently the only source of rt-PA.

Neuroprotective agents are drugs that minimize the effects of the ischemic cascade, and include, for example, Glutamate Antagonists, Calcium Antagonists, Opiate Antagonists, GABA-A Agonists, Calpain Inhibitors, Kinase Inhibitors, and Antioxidants. Several different clinical trials for acute ischemic stroke are in progress. Due to their complementary functions of clot-busting and brain-protection, future acute treatment procedures will most likely involve the combination of thrombolytic and neuroprotective therapies. However, like thrombolytics, most neuroprotectives need to be administered within 6 hours after a stroke to be effective.

Oxygenated Fluorocarbon Nutrient Emulsion (OFNE) Therapy delivers oxygen and nutrients to the brain through the cerebral spinal fluid. Neuroperfusion is an experimental procedure in which oxygen-rich blood is rerouted through the brain as a way to minimize the damage of an ischemic stroke. GPIIb/IIIa Platelet Inhibitor Therapy inhibits the ability of the glycoprotein GPIIb/IIIa receptors on platelets to aggregate, or clump. Rehabilitation/Physical Therapy must begin early after stroke, however, they cannot change the brain damage. The goal of rehabilitation is to improve function so that the stroke survivor can become as independent as possible. L0091 Although some of the acute treatments showed promise in clinical trials, a study conducted in Cleveland showed that only 1.8% of patients presenting with stroke symptoms even received the t-PA treatment (Katzan, et al., Use of tissue-type plasminogen activator for acute ischemic stroke: the Cleveland area experience. JAMA. 2000 Mar. 1; 283(9):1151-1158). t-PA is currently the most widely used of the above-mentioned acute stroke treatments, however, the number of patients receiving any new "effective" acute stroke treatment is estimated to be under 10%. These statistics show a clear need for the availability of acute stroke treatment at greater than 24 hours post stroke.

For some of these acute treatments (i.e., t-PA) the time of administration is crucial. Recent studies have found that the average time of arrival at the hospital is between 3 and 6 hours after stroke (Evenson, et al., Prehospital and in-hospital delays in acute stroke care. Neuroepidemiology. 2001 May; 20(2):65-76) t-PA has been shown to enhance recovery of ~⅓ of the patients that receive the therapy, however a recent study mandated by the FDA (Albers, et al., Intravenous tissue-type plasminogen activator for treatment of stroke: the standard treatment with alteplase to reverse stroke (STARS) study. JAMA. 2000 Mar. 1; 283(9):1 145-50) found that about a third of the time the three-hour treatment window was violated resulting in an ineffective treatment. With the exception of rehabilitation, the remaining acute treatments are still in clinical trials and are not widely available in the U.S., particularly in rural areas, which may not have large medical centers with the needed neurology specialists and emergency room staffing, access to any of these new methods of stroke diagnosis and therapy may be limited for some time.

Human umbilical cord blood (hUCB) may be preferable to other cell sources such as bone marrow due to hUCB cells' low pathogenicity and immune immaturity. The mononuclear cell fraction from human hUCB (MNC hUCB) is relatively rich in multipotent progenitors and has extensive proliferation capacity (Mayani, & Lansdorp, Biology of human umbilical cord blood-derived hematopoietic stem/progenitor cells. Stem Cells. 1998; 16(3):153-165; Todaro, et al., Haematopoietic progenitors from umbilical cord blood. Blood Purif. 2000; 18(2):144-147). A number of studies have shown that intravenously administering MNC hUCB (Saneron's proprietary fraction U-CORD-CELL™). MNC hUCB were hypothesized to provide neuroprotective and/or trophic effects for motor neurons by modulating the host immune inflammatory system through release of various growth or anti-inflammatory factors. Additionally, hUCB plasma (hUCBP) is a rich source of cytokines and other proteins such as insulin-like growth factor-1 (IGF-1), transforming growth factor (TGF)-β and vascular endothelial growth factor (VEGF) required for growth and survival of hematopoietic stem cells (Broxmeyer, et al., Commentary: a rapid proliferation assay for unknown co-stimulating factors in cord blood plasma possibly involved in enhancement of in vitro expansion and replating capacity of human hematopoietic stem/progenitor cells. Blood Cells. 1994; 20 (2-3):492-497; Kim, et al., Ex vivo expansion of human umbilical cord blood-derived T-lymphocytes with homologous cord blood plasma. Tohoku J. Exp. Med. 2005 February; 205(2):115-122; Lam, et al., Preclinical ex vivo expansion of cord blood hematopoietic stem and progenitor cells: duration of culture; the media, serum supplements, and growth factors used; and engraftment in NOD/SCID mice. Transfusion. 2001 December; 41(12):1567-1576). Moreover, it has been shown that hUCB serum contains more neurotrophic factors (substance P, IGF-1, nerve growth factor [NGF]) compared to the peripheral blood serum effectively used for the treatment of the persistent corneal epithelial defects (Vajpayee, et al., Evaluation of umbilical cord serum therapy for persistent conical epithelial defects. Br. J. Ophthalmol. 2003 November; 87(11):1312-1316), neurotrophic keratitis (Yoon, et al., Application of umbilical cord serum eyedrops for the treatment of neurotrophic keratitis. Ophthalmology. 2007 September; 114(9):1637-1642), and recurrent conical erosion (Yoon, et al., Application of umbilical cord serum eyedrops for recurrent conical erosions. Cornea. 2011 July; 30(7):744-748).

Borlongan, et al. (U.S. Pat. No. 7,674,457) provides blood brain barrier permeabilizers, like mannitol, can facilitate entry of stem cells form the periphery into the CNS during acute stages of stroke. However, it was unclear whether BBB permeabilization during chronic stages of stroke also facilitate entry of stem cells from the periphery to the injured brain.

Transplantation of stem cells has been proposed as a means of treating stroke. Neural stem cells are important treatment candidates for stroke and other CNS diseases because of their ability to differentiate in vitro and in vivo into neurons, astrocytes and oligodendrocytes. The powerful multipotent potential of stem cells may make it possible to effectively treat diseases or injuries with complicated disruptions in neural circuitry, such as stroke where more than one cell population is affected.

Despite this great potential, an easily obtainable, abundant, safe, and clinically proven source of stem cells has been elusive until recently. Umbilical cord blood contains a relatively high percentage of hematopoietic stem cells capable of differentiating into all of the major cellular phenotypes of the CNS, including neurons, oligodendrocytes, and glial cells (Sanchez-Ramos, et al., Expression of neural markers in human umbilical cord blood. Exp Neurol. 2001 September; 171(1):109-115; Bicknese, et al., Human umbilical cord blood cells can be induced to express markers for neurons and glia. Cell Transplant. 2002; 11(3):261-264). Following intravenous delivery, human umbilical cord blood (HUCB) cells survive and migrate into the CNS of normal and diseased animals and have been shown to promote functional recovery in animal models of stroke, spinal cord injury, and hemorrhage (Chen, et al., Intravenous administration of human umbilical cord blood reduces behavioral deficits after stroke in rats. Stroke, 2001 November; 32(11): 2682-2688; Lu, et al., Intravenous administration of human umbilical cord blood reduces neurological deficit in the rat after traumatic brain injury. Cell Transplant. 2002; 11(3): 275-281; Saporta, et al., Human umbilical cord blood stem cells infusion in spinal cord injury: engraftment and beneficial influence on behavior. J. Hematother Stem Cell Res. 2003 June; 12(3):271-278).

In addition to the growing body of evidence supporting the neurotherapeutic potential of hUCBC, there is a long and well-established series of practical advantages of using hUCBC for clinical diseases. Cord blood is easily obtained with no risks to the mother or child. A blood sample is taken from the umbilical vein attached to the placenta after birth. The percentage of the primitive stem cells present in the mononuclear fraction is small, but the absolute yield of stem cells available may number in the thousands prior to expansion or other ex vivo manipulation, providing an easily obtainable and plentiful source. Hematopoietic stem cells from hUCB have been routinely and safely used to reconstitute bone marrow and blood cell lineages in children with malignant and nonmalignant diseases after treatment with myeloablative doses of chemoradiotherapy (Lu, et al., Stem cells from bone marrow, umbilical cord blood and peripheral blood for clinical application: current status and future application. Crit Rev Oncol Hematol. 1996 March; 22(2): 61-78; Broxmeyer, ed., Cellular characteristics of cord blood and cord blood transplantation. in press. (AABB Press, 1998, Bethesda, Md.). Early results indicate that a single cord blood sample provides enough hematopoietic stem cells to provide both short- and long-term engraftment. This suggests that these stem cells maintain extensive replicative capacity, which may not be true of hematopoietic stem cells obtained from the adult bone marrow.

SUMMARY OF THE INVENTION

In one embodiment, the method comprises administering cells obtained from umbilical cord blood to an individual in need of treatment, wherein the cells are administered systemically to the individual, and wherein a blood brain barrier permeabilizer is coadministered with the cells. In one embodiment, the cells obtained from human umbilical cord blood comprise a volume reduced cord blood sample. In a further embodiment, the cells obtained from human umbilical cord blood comprise an effective amount of a mononucleated cell.

The present invention further provides for a composition for the treatment of a neurodegenerative disorder. Preferably the neurodegenerative disorder is ischemia, and more preferably, a cerebral infarct. In one embodiment, the composition comprises an effective amount of cell obtained from umbilical cord blood and an effective amount of a blood brain barrier permeabilizer. In a further embodiment, the umbilical cord blood cell is a human umbilical cord blood cell. In one embodiment, the cells obtained from human umbilical cord blood comprise a volume reduced cord blood sample. In a further embodiment, the cells obtained from human umbilical cord blood comprise an effective amount of a mononucleated cell.

In embodiments of the present invention, the blood brain barrier permeabilizer is selected from the group consisting of mannitol; small fat-soluble molecules such as ethanol or ethanol derivatives; and water-soluble molecules such as glucose, mannitol, amino acids, dihydroxyphenylalanine, choline, and purine bases and nucleosides or derivatives thereof. However, other blood brain barrier molecules can be used that are known to those of ordinary skill in the art. In a preferred embodiment, the blood brain barrier permeabilizer is mannitol. In another preferred embodiment, the blood brain barrier permeabilizer is lobradimil (CEREPORT™).

The data herein show evidence that BBB permeabilization in chronic stages of stroke assist in entry of stem cells from the periphery to the stroke brain.

The blood brain barrier permeabilizer is selected from the group consisting of mannitol, lobradimil (CEREPORT™), small fat-soluble molecules, amino acids, dihydroxyphenylalanine, choline, and purine bases and nucleosides or derivatives thereof. Other blood brain barrier permeabilizers can be used that are known to those of ordinary skill in the art.

In one embodiment, the blood brain barrier permeabilizer is mannitol. In another embodiment, the blood brain barrier permeabilizer is lobradimil (CEREPORT™). In one embodiment, the concentration of mannitol is approximately 1.1 M. In other embodiments, mannitol is administered at a concentration of approximately 0.1 mol/L to approximately 10 mol/L, or at a concentration of approximately 0.5 mol/L to approximately 5 mon. In another embodiment, the concentration of lobradimil (CEREPORT™) is approximately 9 pg/kg. In other embodiments, lobradimil (CEREPORT™) is administered at a concentration of approximately 1 pg/kg to approximately 50 µg/kg, or at a concentration of approximately 5 µg/kg to approximately 20 µg/kg.

In one embodiment, the composition is intended for systemic administration to an individual, although other methods for administration are contemplated. In one embodiment the effective amount of the mononucleated cell is approximately $1 \times 10^4$ to approximately $5 \times 10^7$ cells, more preferably is approximately $1 \times 10^5$ to approximately $9 \times 10^6$ cells, more preferably still is approximately $2 \times 10^5$ to approximately $8 \times 10^6$ cells, and most preferably is approximately $2 \times 10^5$ cells. In another embodiment, the effective amount of the mononucleated cell is approximately $0.1 \times 10^6$ cells/kg to approximately $10 \times 10^8$ cells/kg, more preferably is approximately $0.5 \times 10^6$ cells/kg to approximately $5 \times 10^8$ cells/kg, more preferably is approximately $1 \times 10^7$ cells/kg to approximately $2 \times 10^8$ cells/kg, more preferably is approximately $0.5 \times 10^8$ cells/kg, and most preferably is approximately $0.38 \times 10^8$ cells/kg.

The blood brain barrier permeabilizer is selected from the group consisting of mannitol, lobradimil (CEREPORT™), small fat-soluble molecules, glucose, amino acids, dihydroxyphenylalanine, choline, and purine bases and nucleosides or derivatives thereof. Other blood brain barrier permeabilizers can be used that are known to those of ordinary skill in the art. In one embodiment, the blood brain barrier permeabilizer is mannitol. In another embodiment, the blood brain barrier permeabilizer is lobradimil (CEREPORT™). In one embodiment, the concentration of mannitol is approximately 1.1 M. In other embodiments, mannitol is administered at a concentration of approximately 0.1 mol/L to approximately 10 mol/L, or at a concentration of approximately 0.5 mol/L to approximately 5 mon. In another embodiment, the concentration of lobradimil (CEREPORT™) is approximately 9 µg/kg. In other embodiments, lobradimil (CEREPORT™) is administered at a concentration of approximately 1 pg/kg to approximately 50 µg/kg, or at a concentration of approximately 5 µg/kg to approximately 20 µg/kg.

Optionally, the umbilical cord blood cells and blood brain barrier permeabilizer are administered in conjunction with an immunosuppressive agent.

Pharmaceutical compositions comprising effective amounts of umbilical cord blood cells are also contemplated by the present invention. These compositions comprise an effective number of cells, optionally, in combination with a pharmaceutically acceptable carrier, additive or excipient. In certain aspects of the present invention, cells are administered to the patient in need of a transplant in sterile saline. In other aspects of the present invention, the cells are administered in Hanks Balanced Salt Solution (HBSS) or Isolyte 5, pH 7.4. Other approaches may also be used, including the use of serum free cellular media. Systemic administration of the cells to the patient may be preferred in certain indications, whereas direct administration at the site of or in proximity to the diseased and/or damaged tissue may be preferred in other indications.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
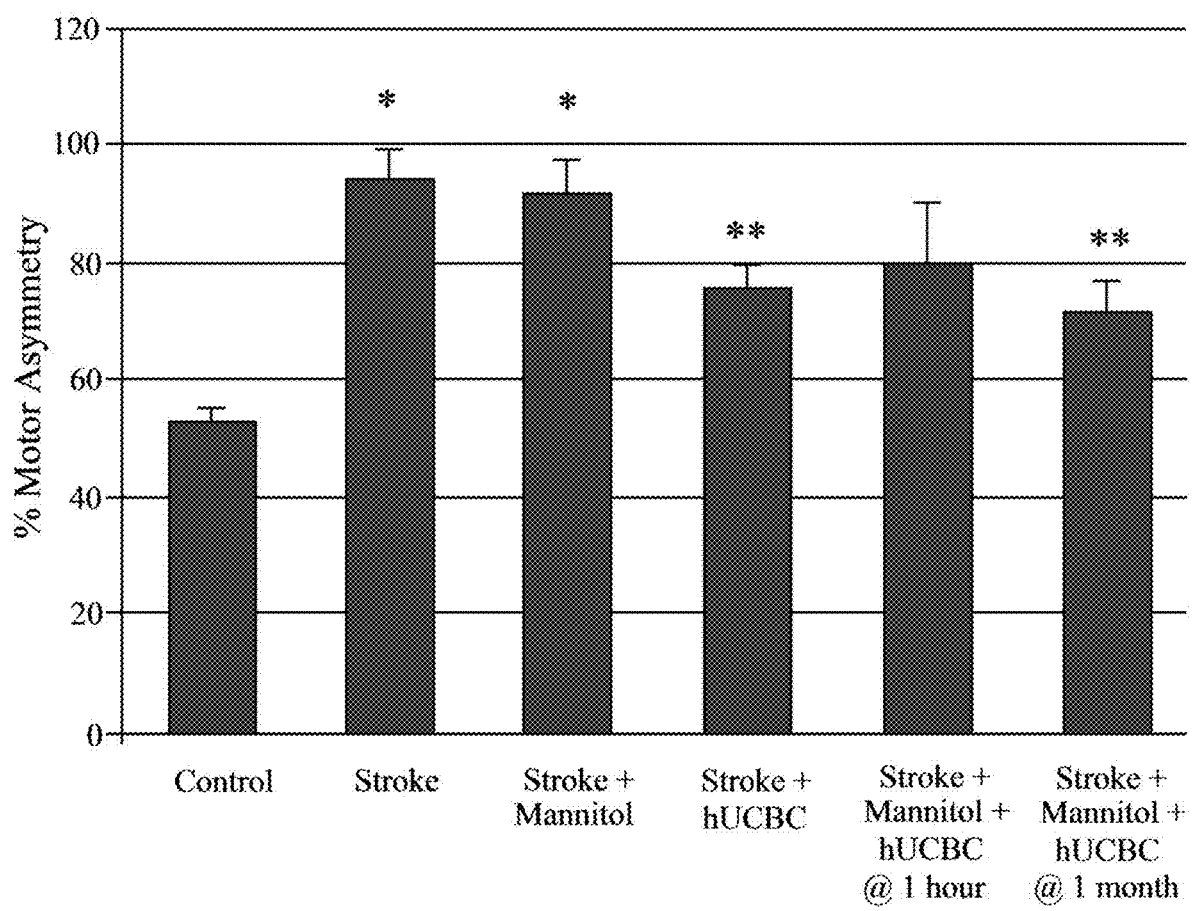
FIG. 1 is a graph showing mannitol's effect on motor function of animals. *$p>0.05$ significantly impaired vs. control. **$p>0.05$ significantly impaired vs. control, but also significantly recovered compared to stroke (vehicle only) and stroke with mannitol.

As used herein, "treat", "treatment", "treating", and the like refer to acting upon a condition, such as a neurodegenerative disease, with an agent depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as antibodies or other agents which are effective for producing an intended result, including preventing further autoimmune disease or immunotolerance, or treating an autoimmune disease, such as rheumatoid arthritis and asthma, or immunotolerance, such as cancer. Compositions according to the present invention may be used to effect a favorable change on immune cells, whether that change is an improvement, such as stopping or reversing the immune disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into a patient. One preferred route of administration of the agent is oral administration. Another preferred route is intravenous administration. However, any route of administration, such as subcutaneous, peritoneal, intraarterial, introduction into the cerebrospinal fluid, or instillation into body compartments can be used.

As used herein, the term "blood brain barrier permeabilizer" is a substance that is capable of disrupting the blood brain barrier. In one embodiment, the disruption is temporary. The amount of blood brain barrier permeabilizer administered with the umbilical cord blood cells is the amount effective to disrupt the blood brain barrier and allow neurotrophic growth factors to enter the brain in increased amounts and/or allow the cells obtained from HLJCB to enter the brain. In one embodiment of the present invention, the blood brain barrier permeabilizer allows increased entry of neurotrophic factors into the brain when measured with 0-10 days after administration.

As used herein, the term "subject," "patient," or "organism" includes humans and mammals (e.g., mice, rats, pigs, cats, dogs, and horses). Typical patients to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The term "umbilical cord blood" is used herein to refer to blood obtained from a neonate or fetus, most preferably a neonate and preferably refers to blood that is obtained from the umbilical cord or the placenta of newborns. Preferably, the umbilical cord blood is isolated from a human newborn.

The use of umbilical cord blood as a source of mononuclear cells is advantageous because it can be obtained relatively easily and without trauma to the donor. Umbilical cord blood cells can be used for autologous transplantation or allogenic transplantation, when and if needed. Umbilical cord blood is preferably obtained by direct drainage from the cord an/or by needle aspiration from the delivered placenta at the root and at distended veins. As used herein, the term "cells obtained from umbilical cord blood" refers to cells that are present within umbilical cord blood. In one embodiment, the cells obtained from umbilical cord blood are mononucleated cells that are further isolated from the umbilical cord blood.

In another embodiment, the cells obtained from umbilical cord blood comprise a volume reduced cord blood sample. The production of a volume reduced cord blood sample is well-known to those of skill in the art. One non-limiting method for producing a volume reduced cord blood sample is adding Hespan in a 1:5 ratio to whole HUCB to the original collection bag, gently mixing the contents of the bag, and centrifuging the contents. After centrifugation, the blood bag is allowed to sit for 15 minutes in a closed plasma extractor. The buffy coat is transferred to a new Processing bag and centrifuged. The plasma is expressed and the remaining buffy coat is cooled for 15 minutes. A 50% DMSO:5% Gentran 40 mixture is slowly added to the buffy coat and gently mixed. The cells are transferred to a Freezing bag and the cells are cryogenically frozen in a computer-controlled step down freezer. In further embodiments, the cells obtained from umbilical cord blood comprise cells that are effective for producing the intended result of treating a neurodegenerative disease.

The invention is further directed to a method of treating a neurodegenerative disease, comprising administering an effective amount of cells obtained from human umbilical cord blood and an effective amount of a blood brain barrier permeabilizer to an individual with a neurodegenerative disease. In one embodiment, the cells obtained from human umbilical cord blood comprise a volume reduced cord blood sample. In a further embodiment, the cells obtained from human umbilical cord blood comprise an effective amount of a mononucleated cell. Preferably the individual is a human. In one embodiment, the mononucleated cell is frozen after being obtained from human umbilical cord blood and is thawed prior to administration to the individual.

The umbilical cord blood cells are administered with a blood brain barrier permeabilizer. In one embodiment, the cells are combined with the permeabilizer prior to administration into the patient. In another embodiment, the cells are administered separately to the patient from the permeabilizer. Optionally, if the cells are administered separately from the permeabilizer, there is a temporal separation in the administration of the cells and the permeabilizer. The temporal separation may range from about less than a minute in time, to about hours or days in time. The determination of the optimal timing and order of administration is readily and routinely determined by one of ordinary skill in the art.

Example 1 hUCB was collected immediately after infant delivery. The umbilical cord was double clamped as per normal standard of care and the cord wiped with 70% alcohol and betadine at the needle insertion (collection) site, which was just proximal to the clamp that remains on the cord. The 16-gauge, ultra-thin wall needle was inserted into the umbilical cord and held in place. The blood was allowed to flow into the attached collection bag, normally 3-5 minutes (the placenta & cord could be elevated slightly to increase the volume of blood collected) with about 50-100 mL of hUCB collected. Once collection was complete, 2-3 knots were tied in the collection tubing to prevent leakage and the bag was gently inverted to mix the cord blood with citrate-phosphate-dextrose (CPD) anticoagulant. The collection bag was placed into a plastic bag and secured to the bottom of the collection kit container, which was then sealed. The sample was stored at 1 5°-25° C. until processing.

The umbilical cord blood was processed within 48 hours of collection. Blood cell counts [nucleated, mononucleated, $CD34^+$, red blood, colony forming unit, granulocyte, monocyte, lymphocyte, and platelet cell counts (total count and percentage)] were taken prior to start of processing. Gradient separation of the mononucleated fraction (MNF) from the plasma was performed using Ficoll-hypaque at 400×g for 30 minutes. The MNF was collected and washed 3 times with RPMI-1640 (Gibco BRL) at 400×g for 30 minutes. Blood cell counts were repeated and viability was determined. Processed samples were considered acceptable if the sample had $2\times10^7$ or more cells and 95% or more viability. hUCB cells were placed in 1 mL of cryopreservation freezing media (90% Autologous Plasma, 10% DMSO). The hUCB cells were then cryogenically frozen in a computer-controlled step down freezer at a rate of −1° C./minute to −80° C. The hUCB cells were transferred to the vapor phase of liquid $N_2$. The cells remained in this cryogenic quarantine until results of the infectious disease testing were known (approximately 4 weeks).

Example 2

Sprague Dawley rats were housed in pairs in polycarbonate cages with food and water available ad libitum in a temperature-controlled room (22° C.+/−3° C., 12-hour light-dark cycle).

All surgical procedures were conducted under aseptic conditions. Anesthetized (equithesin 300 mg/kg i.p.) animals were subjected to the middle cerebral artery occlusion (MCAO) model using a well-established embolic technique that occludes the right MCA. Based on prior studies (Borlongan, et al., Transplantation of cryopreserved human embryonal carcinoma-derived neruons (NT2N Cells) promotes functional recovery in ishemic rats. Exp Neurol. 1998 February; 149(2): 310-321; Borlongan, et al., Locomotor and passive avoidance deficits following occlusion of the middle cerebral artery. Physiol Behav. 1995 November; 58(5):909-917; Borlongan, et al., Striatal dopamine-mediated motor behavior is altered following occlusion of the middle cerebral artery. Pharmacol Biochem Behav. 1995 September; 52(1):225-22), a one-hour occlusion of the MCA was observed to result in maximal infarction. In addition, the length (15-17 mm) and size of the tip (24-26 gauge) of the embolus were found to produce complete MCAO in animals weighing between 250 and 350 g. A heating pad and a rectal thermometer allow maintenance of body temperature at normal limits during the surgery. To ensure similar degree of stroke insults among animals, $PaO_2$, $PaCO_2$ and plasma pH measurements were monitored in each animal (Chang, et al., Hyperbaric oxygen therapy for treatment of postischemic stroke in adult rats. Exp Neurol. 2000 December; 166(2):298-306). In addition, to ensure successful arterial occlusion, a Laser Doppler was used to monitor cerebral blood flow (Wang, et al., Methamphetamine potenitaets ischemia/reperfusion insults after transient middle cerebral artery ligation. Stroke. 2001 March; 32(3):775-782).

Following surgery, animals were placed in clean, warmed cages until they gained consciousness, at which time they were returned to the animal colony room. Food and water were freely accessible at a lowered height in their cages. Animals were given antibiotics and analgesics for 3 days after surgery.

Example 3

The histological and neurobehavioral effects of early intracerebral and intraarterial delivery of hUCB cells into rats during transient middle cerebral artery occlusion (MCAO) were examined Twenty-six adult male Sprague Dawley rats were subjected to right MCAO for 60 minutes, as discussed in Example 2. During the one-hour occlusion, hUCBC, as processed in Example 1, were prepared for injection.

The hUCBC (Saneron CCEL Therapeutics, Inc., Tampa, Fla.) were thawed at 37° C. Cells were washed and centrifuged three times (1000 rpm for 7 minutes). Viability was determined using the trypan blue dye exclusion method and cell concentration was adjusted to 10,000 cells/µl. A minimum of 85% viability post-thaw was required for a sample to be used for transplantation Immediately after the one-hour occlusion of the MCA, 200,000 hUCB cells, suspended in 10 µl solution in a 28-gauge Hamilton syringe, were injected intra-arterially using the same internal carotid artery where the embolic filament was previously inserted. Infusion rate was 1 µl per minute as determined by using a micro-infusion pump. A blood brain barrier permeabilizer (1.1 M mannitol at 4° C.) was administered immediately after hUCBC injection.

Behavioral tests were conducted on post-stroke day 3, prior to sacrificing animals for histology to determine lesion volumes and hUCB cell survival. Separate sets of identically treated animals were used to measure brain levels of glial cell line-derived neurotrophic factor (GDNF), nerve growth factor (NGF), and brain-derived neurotrophic factor (BDNF) were measured by enzyme-linked immunosorbent assay (ELISA).

Stroke rats exhibit deficits in locomotor behavior and neurological functions, display motor asymmetry (i.e., since animals received unilateral MCAO, bias movements to one side of the body is displayed), and are impaired in cognitive performance (Borlongan, et al., Transplantation of cyropreserved human embryonal carcinoma-derived neruons (NT2N Cells) promotes functional recovery in ishemic rats. Exp Neurol. 1998 February; 149(2): 310-321; Borlongan, et al., Locomotor and passive avoidance deficits following occlusion of the middle cerebral artery. Physiol Behav. 1995 November; 58(5):909-917; Borlongan, et al., Striatal dopamine-mediated motor behavior is altered following occlusion of the middle cerebral artery. Pharmacol Biochem Behav. 1995 September; 52(1):225-22; Borlongan, et al., Viability and survival of hNT neurons determine degree of functional recovery in grafted ischemic rats. Neuroreport. 1998 Aug. 24; 9(12):2837-2842; Borlongan, et al., Cerebral ischemia and CNS transplantation: differential effects of grafted fetal rat striatal cells and human neurons derived from a clonal cell line. Neuroreport. 1998 Nov. 16; 9(16): 3703-3709; Roof, et al., A comparison of long-term functional outcome after 2 middle cerebral artery occlusion models in rats. Stroke. 2001 November; 32(11):2648-57). Thus, the present behavioral tests involve quantitative analyses of general locomotor behavior (using the Accuscan locomotor activity monitor apparatus), examination of neurological functions (Bederson test), semi-quantitative analysis of motor asymmetry (elevated body swing test, EBST), and quantitative analysis of performance in a cognitive task (step-down shuttle box passive avoidance test). The choice of weekly behavioral assessment was based on previous studies indicating that stroke symptoms become apparent as early as one week after stroke and are stable over a month and sustained up to at least 6 months post-stroke (Borlongan, et al., Transplantation of cryopreserved human embryonal carcinoma-derived neruons (NT2N Cells) promotes functional recovery in ishemic rats. Exp Neurol. 1998 February; 149(2): 310-321; Borlongan, et al., Locomotor and passive avoidance deficits following occlusion of the middle cerebral artery. Physiol Behav. 1995 November; 58(5):909-917; Borlongan, et al., Striatal dopamine-mediated motor behavior is altered following occlusion of the middle cerebral artery. Pharmacol Biochem Behav. 1995 September; 52(1):225-229; Chang, et al., Hyperbaric oxygen therapy for treatment of postischemic stroke in adult rats. Exp Neurol. 2000 December; 166(2):298-306; Borlongan, et al., Viability and survival of hNT neurons determine degree of functional recovery in grafted ischemic rats. Neuroreport. 1998 Aug. 24; 9(12):2837-2842; Borlongan, et al., Cerebral ischemia and CNS transplantation: differential effects of grafted fetal rat striatal cells and human neurons derived from a clonal cell line. Neuroreport. 1998 Nov. 16; 9(16):3703-3709; Roof, et al., A comparison of long-term functional outcome after 2 middle cerebral artery occlusion models in rats. Stroke. 2001 November; 32(11):2648-57; Chiang, et al., Transplantation of fetal kidney tissue reduces cerebral infarction induced by middle cerebral artery ligation. J Cereb Blood Flow Metab. 1999 December; 19(12):1329-1335; Johnston, et al., Trophic factor secreting kidney cell lines: in vitro characterization and functional effects following transplantation in ischemic rats. Brain Res. 2001 May 11; 900(2):268-276). These tests have been shown to be sensitive assays of behavioral deficits produced by unilateral MCAO stroke surgery (Aihara, et al., Striatal grafts in infarct striatopallidum increase GABA release, reorganize GABAA receptor and improve water-maze learning in the rat. Brain Res Bull. 1994; 33(5):483-488; Borlongan, et al., Transplantation of cryopreserved human embryonal carcinoma-derived neruons (NT2N Cells) promotes functional recovery in ishemic rats. Exp Neurol. 1998 February; 149 (2): 310-321; Borlongan, et al., Locomotor and passive avoidance deficits following occlusion of the middle cerebral artery. Physiol Behav. 1995 November; 58(5):909-917; Borlongan, et al., Striatal dopamine-mediated motor behavior is altered following occlusion of the middle cerebral artery. Pharmacol Biochem Behav. 1995 September; 52(1):225-22; Roof, et al., A comparison of long-term functional outcome after 2 middle cerebral artery occlusion models in rats. Stroke. 2001 November; 32(11):2648-57; Borlongan & Sanberg, Elevated body swing test: a new behavioral parameter for rats with 6-hydroxydopamine-induced hemiparkinsonism. J Neurosci. 1995 July; 15 (& Pt 2):5372-5378; Nishino & Borlongan, Restoration of function by neural transplantation in the ischemic brain. Frog Brain Res. 2000; 127:461-476; Nishino, et al., Striatal grafts in the ischemic straitum improve pallidal GABA release and passive avoidance. Brain Res Bull. 1993; 32(5):517-520). Animals were randomly subjected in the 4 tests mentioned above.

The Accuscan locomotor activity test is a sensitive behavioral test for determining the extent of MCAO-induced cerebral ischemia (Chang, et al., Intravenous administration of bone morphogenetic protein-7 after ischemia improves motor function in stroke rats. Stroke. 2003 February; 34(2): 558-564; Borlongan, et al., Locomotor and passive avoidance deficits following occlusion of the middle cerebral artery. Physiol Behav. 1995 November; 58(5):909-917; Borlongan, et al., Striatal dopamine-mediated motor behavior is altered following occlusion of the middle cerebral artery. Pharmacol Biochem Behav. 1995 September; 52(1):225-22). For the Accuscan locomotor activity test, animals were tested at nighttime. The following locomotor variables were measured: horizontal activity, total distance, number of movements, movement time, rest time, speed, vertical activity, vertical movements, vertical time, stereotypy counts, number of stereotypies, stereotypy time, clockwise rotations and anti-clockwise rotations. Data were collected every hour for 12 consecutive hours (6 PM to 6 AM).

The Bederson test is conducted following the procedures previously described (Altumbabic & Del Bigio, Transplantation of fetal brain tissue into the site of intracerebral hemorrhage in rats. Neurosci Lett. 1998 Nov. 27; 257(2): 61-64). Neurologic score for each rat was obtained using 4 tests which include (1) observation of spontaneous ipsilateral circling, graded from 0 (no circling) to 3 (continuous circling); (2) contralateral hindlimb retraction, which measures the ability of the animal to replace the hindlimb after it is displaced laterally by 2 to 3 cm, graded from 0 (immediate replacement) to 3 (replacement after minutes or no replacement); (3) beam walking ability, graded 0 for a rat that readily traverses a 2.4-cm-wide, 80-cm-long beam to 3 for a rat unable to stay on the beam for 10 seconds; and (4) bilateral forepaw grasp, which measures the ability to hold onto a 2-nmi-diameter steel rod, graded 0 for a rat with normal forepaw grasping behavior to 3 for a rat unable to grasp with the forepaws. The scores from all 4 tests, which were done over a period of about 15 minutes on each assessment day, were added to give a neurologic deficit score (maximum possible score, 12).

The EBST involves handling the animal by its tail and recording the direction of the swings. The test apparatus consisted of a clear Plexiglas box (40×40×35.5 cm). The animal was gently picked up at the base of the tail, and elevated by the tail until the animal's nose was at a height of 2 inches (5 cm) above the surface. The direction of the swing, either left or right, was counted once the animals head moved sideways approximately 10 degrees from the midline position of the body. After a single swing, the animal was placed back in the Plexiglas box and allowed to move freely for 30 seconds prior to retesting. These steps were repeated 20 times for each animal. Normally, intact rats display a 50% swing bias, that is, the same number of swings to the left and to the right. A 75% swing bias indicates 15 swings in one direction and 5 in the other during 20 trials. The EBST was previously utilized, and it was noted that MCAO stroke animals display >75% biased swing activity as early as the day of stroke surgery (i.e., after recovery from anesthesia), and such motor asymmetry is stable for up to six months (Borlongan, et al., Locomotor and passive avoidance deficits following occlusion of the middle cerebral artery. Physiol Behav. 1995 November; 58(5):909-917; Borlongan, et al., Striatal dopamine-mediated motor behavior is altered following occlusion of the middle cerebral artery. Pharmacol Biochem Behav. 1995 September; 52(1):225-229).

Animals were introduced to passive avoidance testing as described in detail elsewhere (Borlongan, et al., Viability and survival of hNT neurons determine degree of functional recovery in grafted ischemic rats. Neuroreport. 1998 Aug. 24; 9(12):2837-2842). Briefly, training and testing were carried out using a step-down passive avoidance box (27× 27×30 cm; Lafayette Inst. Co.) made of Plexiglas. A Plexiglas platform shelf (7.5×26.7×9.4 cm) is located in one corner of the box. Upon stepping off the platform, the rat received scrambled foot shock (approximately 2 mA; generated by a DC shock scrambler BRS Foringer No. SCS-003). Acquisition of the task is measured in terms of the amount of time it took the rat to remain on the platform continuously for 3 minutes. Twenty-four hours later, a retention test was conducted by placing the rat on the platform exactly as before and recording the latency to step-down measured to a maximum of 3 minutes. MCAO stroke animals display significant impairments in acquisition and retention of the task as early as 24 hours post-ischemia that persist at least up to 6 months post-ischemia (Chen, et al., Intravenous administration of human umbilical cord blood reduces behavioral deficits after stroke in rats. Stroke, 2001 November; 32(11):2682-2688; Borlongan, et al., Cerebral ischemia and CNS transplantation: differential effects of grafted fetal rat striatal cells and human neurons derived from a clonal cell line. Neuroreport. 1998 Nov. 16; 9(16): 3703-3709).

Behavioral tests of both motor and cognitive function were conducted at a single early time point post stoke (i.e., day 3) to determine if combining hUCB cells with mannitol would produce more immediate and robust effects. Stroke-induced motor deficits, measured by percent motor asymmetry using the elevated swing bias test, were significantly reduced by 15% when hUCB cells were combined with mannitol and administered intra-arterially (p<0.05). Cognitive deficits measured by time to acquisition of a passive avoidance task showed a trend towards a reduction in acquisition time (p=0.072) and an analysis of memory of this same task revealed a significant 20% increase in retention time with intra-arterial administration (p<0.05). These benefits were not seen with hUCB-only transplants, i.e. no benefits were observed relative to animals receiving stroke only. Thus, the combination of hUCB cells with mannitol produced an impressive profile of behavioral recovery.

While behavioral recovery has been consistently reported using hUCB cells in stroke animal tests have shown that intra-arterial and intravenous delivery of hUCB during MCA occlusion also limited volume of infarcted tissue and promoted neuroprotection, but only when combined with mannitol. Animals treated with hUCB cells and mannitol showed a statistically significant (p<0.05, ANOVA) 40% reduction in the size of infarction. The decrease in lesion volume 3 days after MCAO suggests that the hUCB cells are either exerting a direct trophic effect on the damaged tissue or are elevating endogenous levels of trophic activity. Replicating the above data, separate studies again confirmed that combining hUCB cells with mannitol produced a significant neuroprotective effect. These studies also revealed associated elevations of brain levels of GDNF (increased 68% above controls).

Example 4

Work has shown that blood brain barrier (BBB) permeabilizers, such as mannitol, can facilitate the entry of stem cells from the periphery to the stroke brain, as seen in Example 3. However, these studies were limited to BBB permeation in the acute stage of stroke. Whether BBB permeation in the chronic stage of the disease still facilitates the entry of stem cells from the periphery to the injured brain remains to be investigated.

Adult Sprague-Dawley rats initially received sham surgery or experimental stroke via the one-hour middle cerebral artery occlusion (MCAO) model, as disclosed in Example 2. At 1 month after the MCAO surgery, stroke animals were randomly assigned to receive human umbilical cord stem cells only (2 million viable cells), mannitol only (1.1 mol/L mannitol at 4° C.), combined human umbilical cord stem cells (200,000 viable cells) and mannitol (1.1 mol/L mannitol at 4° C.), and vehicle (phosphate buffered saline, PBS) only.

The hUCBC (Saneron CCEL Therapeutics, Inc., Tampa, Fla.) were thawed at 37° C. Cells were washed and centrifuged three times (1000 rpm for 7 minutes). Viability was determined using the trypan blue dye exclusion method and cell concentration was adjusted to 10,000 cells/µl. A minimum of 85% viability post-thaw was required for a sample to be used for transplantation. For hUCBC+BBB, 200,000 hUCB cells were suspended in 10 µl PBS in a 28-gauge Hamilton syringe. For hUCBC only, $2\times10^6$ cells were suspended in XX µl PBS. The BBB only treatment was injected as prepared. Treatments were administered by intra-arterial injection into the internal carotid artery where the embolic filament was previously inserted. Infusion rate was 1 µl per minute as determined by using a micro-infusion pump.

Vehicle- and mannitol-treated stroke rats displayed significant deficits in behavioral (motor abnormalities), as seen in FIG. 1. Vehicle-treated rats displayed a high degree of motor asymmetry, near 100%. Addition of mannitol lowered the motor asymmetry slightly, which did not differ significantly from vehicle-only treatment. Treatment with hUCBC lowered motor asymmetry for around 75%, which differed significantly from vehicle-only and mannitol-treated rats. Adding a BBB to the hUCBC further decreased motor asymmetry to around 70%.

Figure 2:
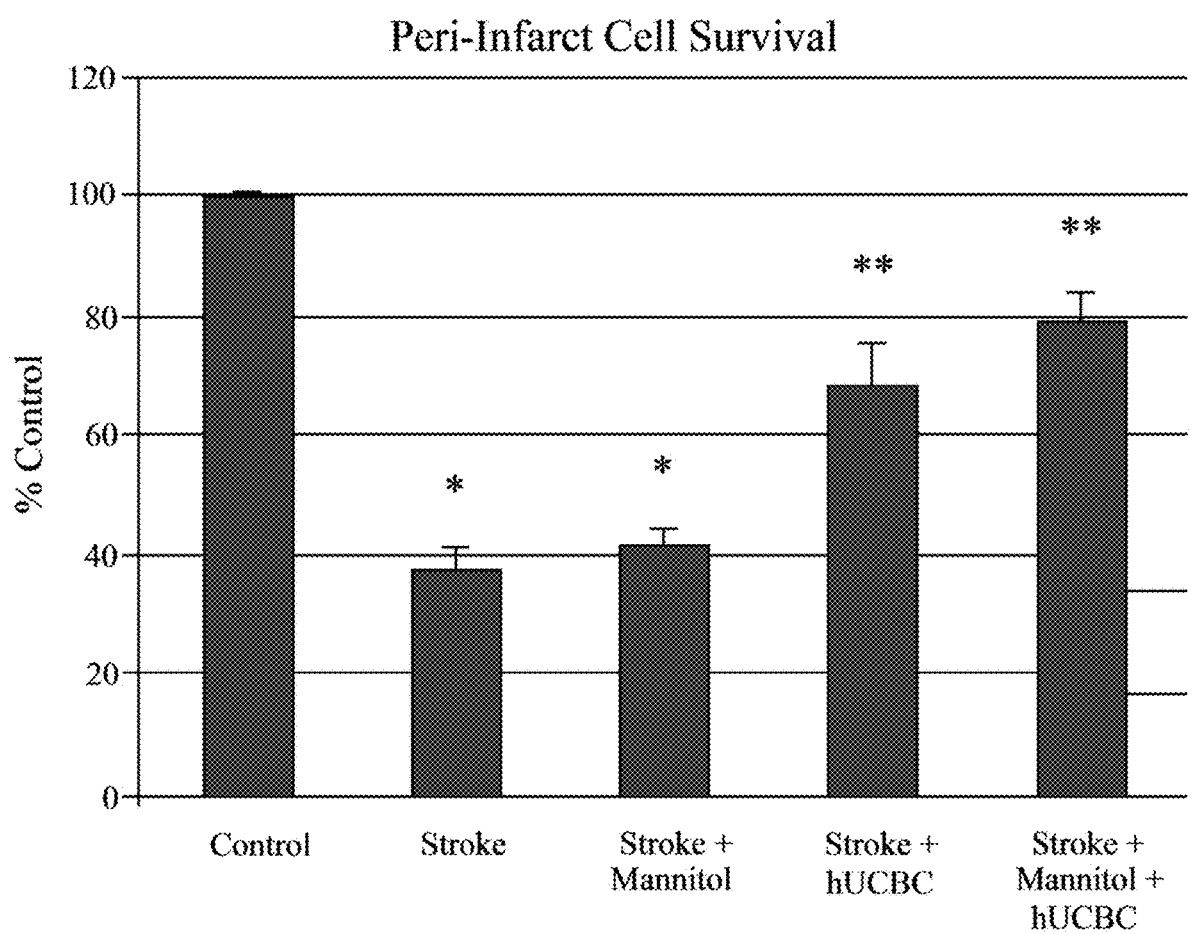
FIG. 2 is a graph showing mannitol's effect on transplanted stem cell transport from the periphery on cell survival. *$p>0.05$ significantly impaired vs. control. **$p>0.05$ significantly impaired vs. control, but also significantly recovered compared to stroke (vehicle only) and stroke with mannitol.

Histological analysis showed rats treated with BBB only exhibited significant brain damage compared to sham surgery animals (control), as seen in FIG. 2. However, in rats treated with hUCBC only, damage to the brain was significantly improved, though not to the level of sham-operated rats. Administering hUCBC and BBB (mannitol) to MCAO-treated rats decreased damage beyond the levels found with hUCBC only, from around 70% cell survival with hUCBC only to almost 80% with hUCBC and BBB.

Figure 3A:
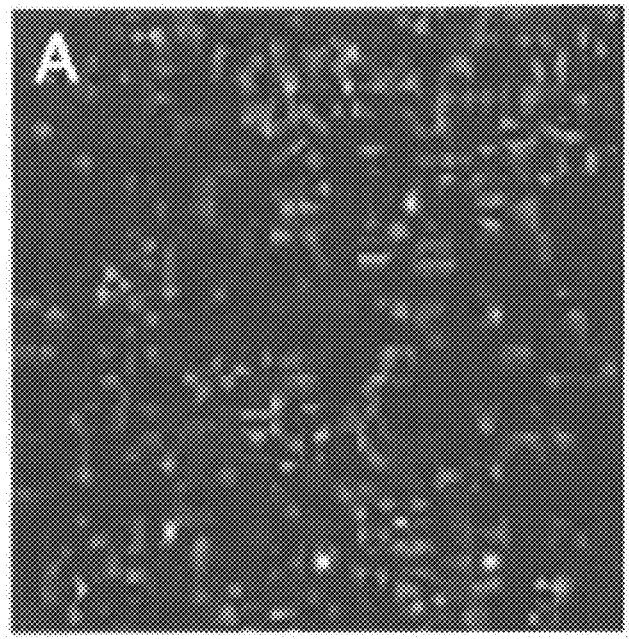
FIG. 3(A) shows images of histochemistry immunofluorescence of cells from the cerebral cortex treated with stem cells. Cells were stained with DAPI and imaged at 20×.
Figure 3B:
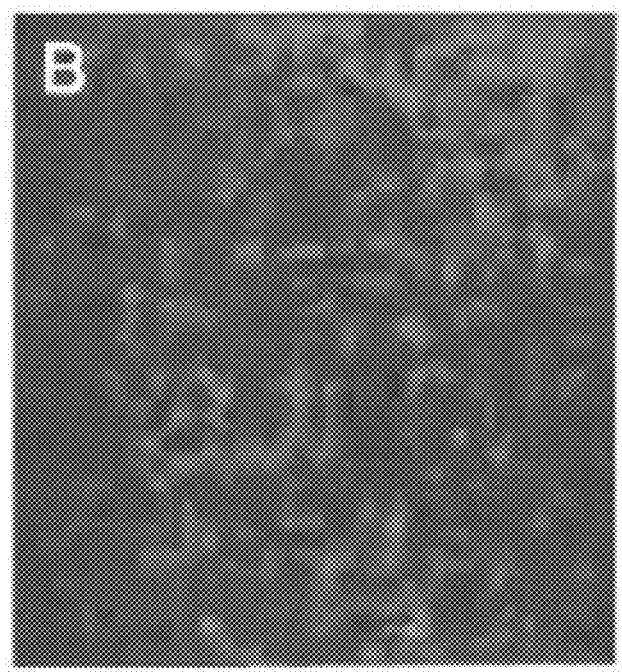
FIG. 3(B) shows images of histochemistry immunofluorescence of cells from the cerebral cortex treated with stem cells. Cells were stained with DCX and imaged at 20×.
Figure 3C:
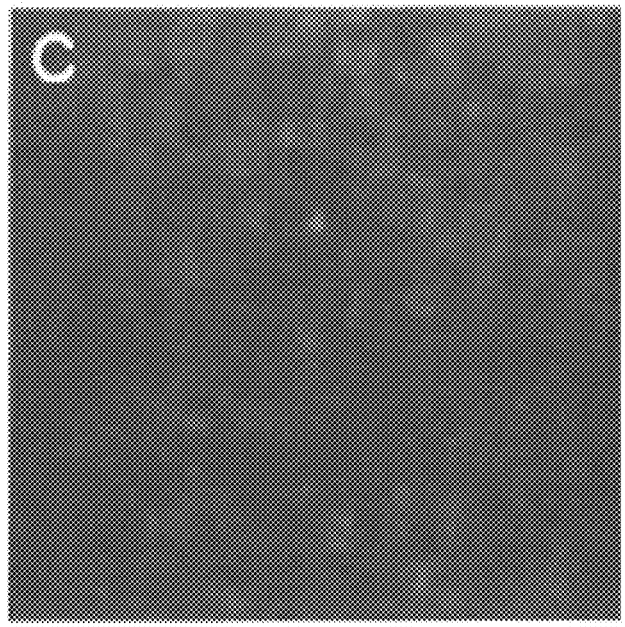
FIG. 3(C) shows images of histochemistry immunofluorescence of cells from the cerebral cortex treated with stem cells. Cells were stained with HuNu and imaged at 20×.
Figure 3D:
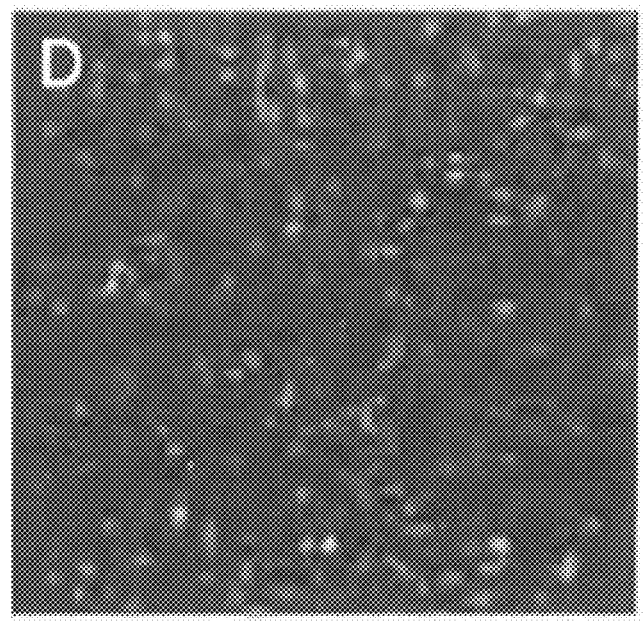
FIG. 3(D) shows images of histochemistry immunofluorescence of cells from the cerebral cortex treated with stem cells. Cells were stained with DAPI, DCX, and HuNu, and merged images collected at 20×.
Figure 4A:
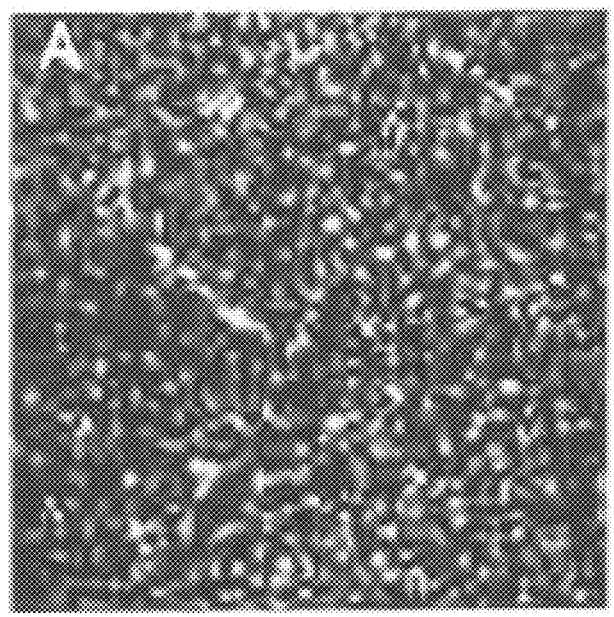
FIG. 4(A) shows images of histochemistry immunofluorescence of cells from the cerebral cortex treated with stem cells and mannitol. Cells were stained with DAPI and imaged at 20×.
Figure 4B:
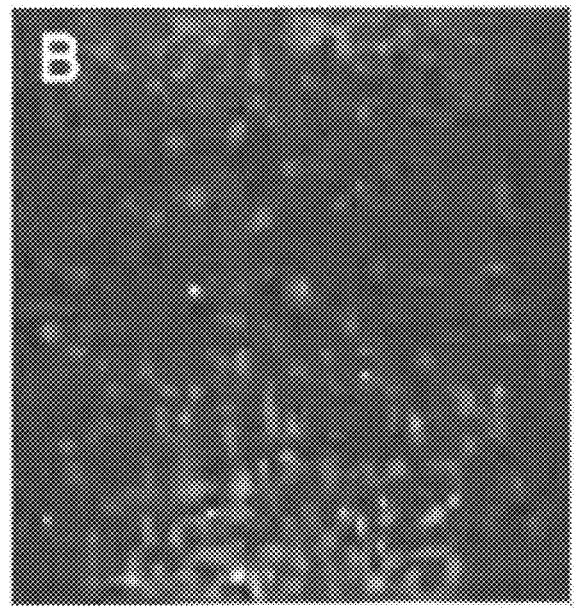
FIG. 4(B) shows images of histochemistry immunofluorescence of cells from the cerebral cortex treated with stem cells and mannitol. Cells were stained with DCX and imaged at 20×.
Figure 4C:
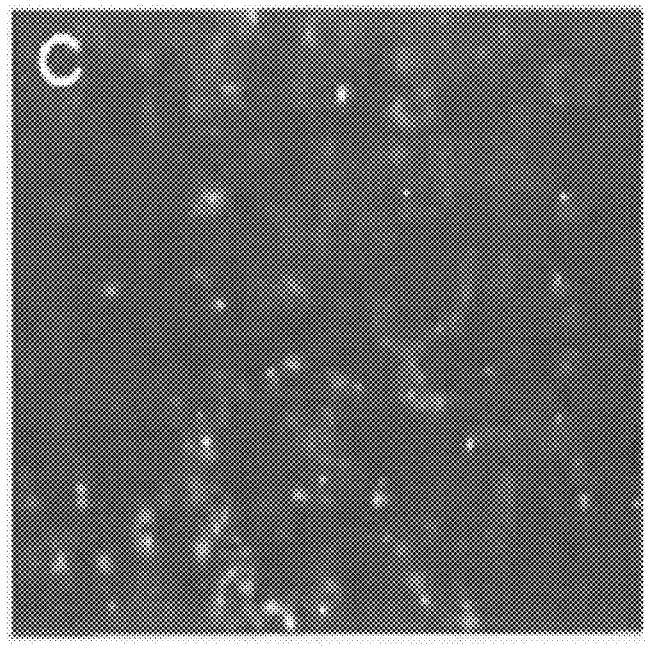
FIG. 4(C) shows images of histochemistry immunofluorescence of cells from the cerebral cortex treated with stem cells and mannitol. Cells were stained with HuNu and imaged at 20×.
Figure 4D:
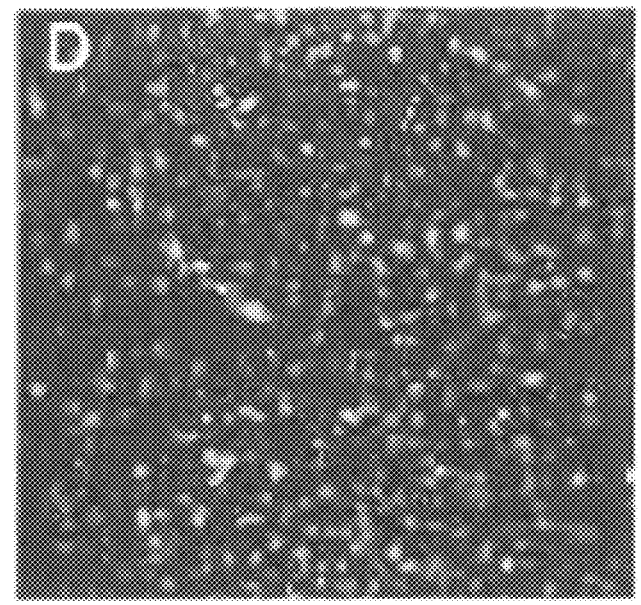
FIG. 4(D) shows images of histochemistry immunofluorescence of cells from the cerebral cortex treated with stem cells and mannitol. Cells were stained with DAPI, DCX, and HuNu, and merged images collected at 20×.
Figure 5A:
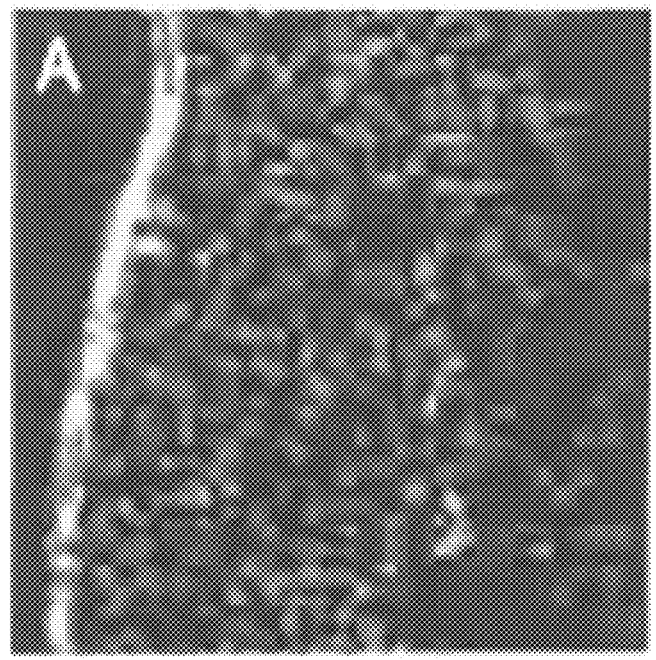
FIG. 5(A) shows images of histochemistry immunofluorescence of cells from the subventricular zone treated with stem cells. Cells were stained with DAPI and imaged at 20×.
Figure 5B:
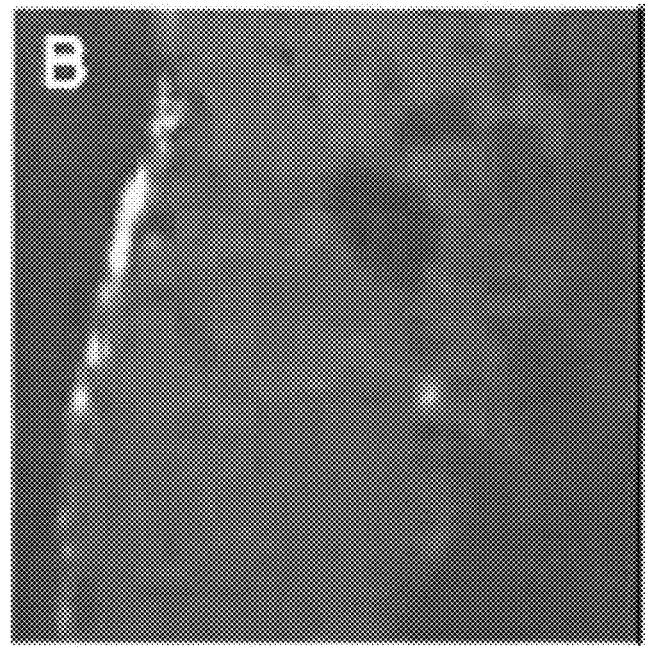
FIG. 5(B) shows images of histochemistry immunofluorescence of cells from the subventricular zone treated with stem cells. Cells were stained with DCX and imaged at 20×.
Figure 5C:
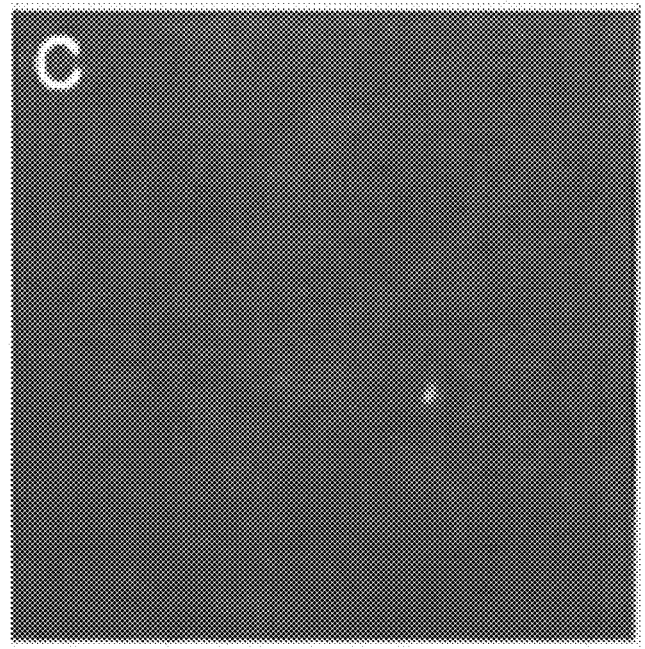
FIG. 5(C) shows images of histochemistry immunofluorescence of cells from the subventricular zone treated with stem cells. Cells were stained with HuNu and imaged at 20×.
Figure 5D:
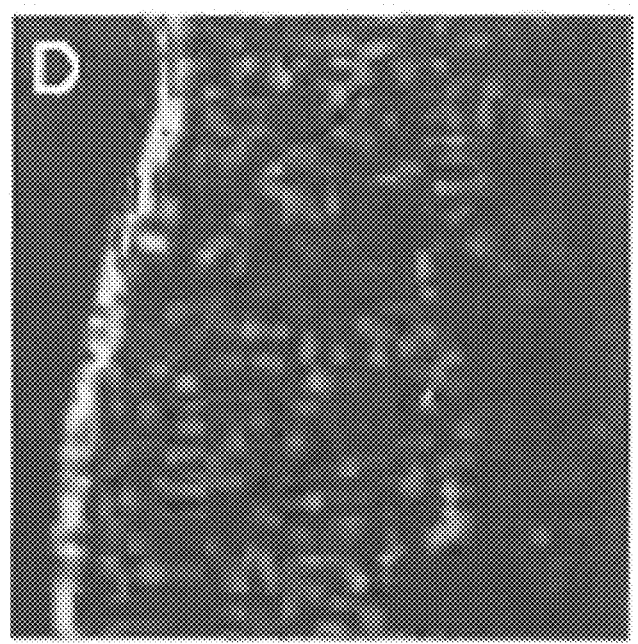
FIG. 5(D) shows images of histochemistry immunofluorescence of cells from the subventricular zone treated with stem cells. Cells were stained with DAPI, DCX, and HuNu, and merged images collected at 20×.
Figure 5E:
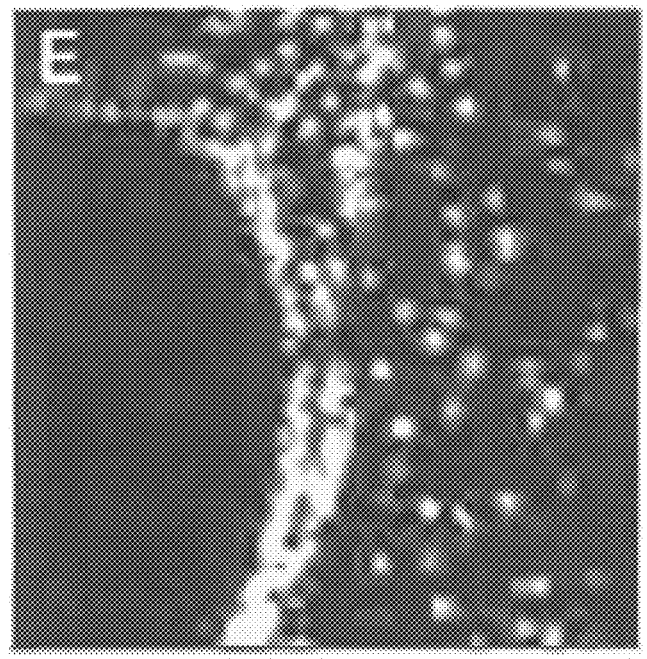
FIG. 5(E) shows images of histochemistry immunofluorescence of cells from the subventricular zone treated with stem cells. Cells were stained with DAPI and imaged at 40×.
Figure 5F:
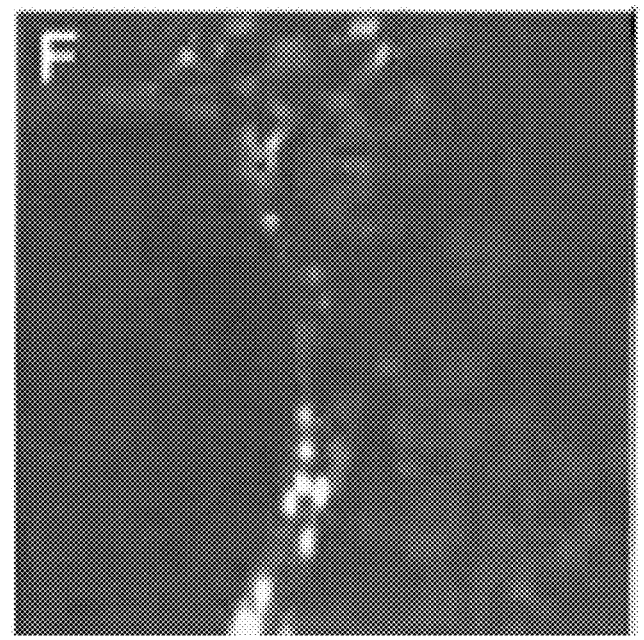
FIG. 5(F) shows images of histochemistry immunofluorescence of cells from the subventricular zone treated with stem cells. Cells were stained with DCX and imaged at 40×.
Figure 5G:
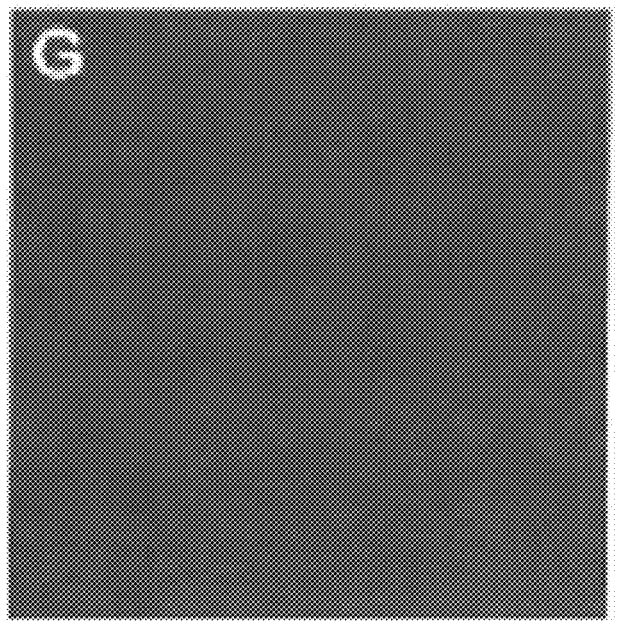
FIG. 5(G) shows images of histochemistry immunofluorescence of cells from the subventricular zone treated with stem cells. Cells were stained with HuNu and imaged at 40×.
Figure 5H:
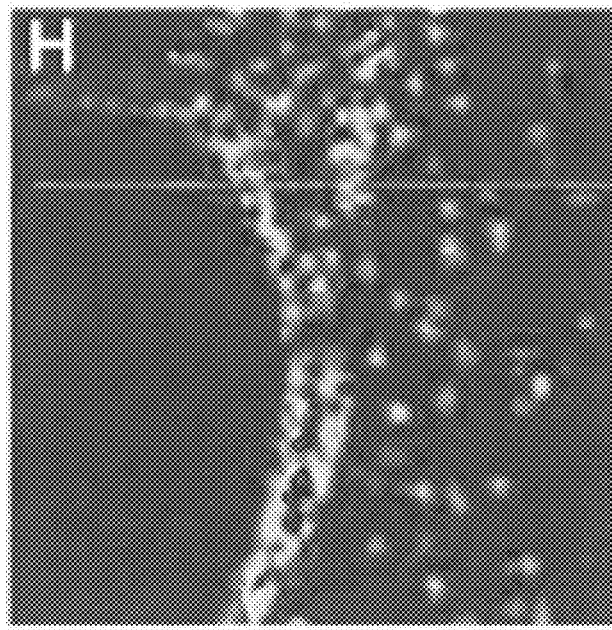
FIG. 5(H) shows images of histochemistry immunofluorescence of cells from the subventricular zone treated with stem cells. Cells were stained with DAPI, DCX, and HuNu, and merged images collected at 40×.
Figure 6A:
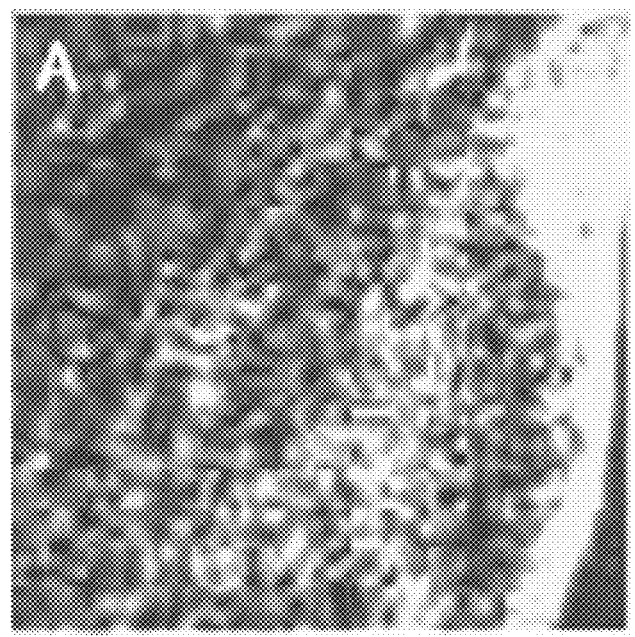
FIG. 6(A) shows images of histochemistry immunofluorescence of cells from the subventricular zone treated with stem cells and mannitol. Cells were stained with DAPI and imaged at 20×.
Figure 6B:
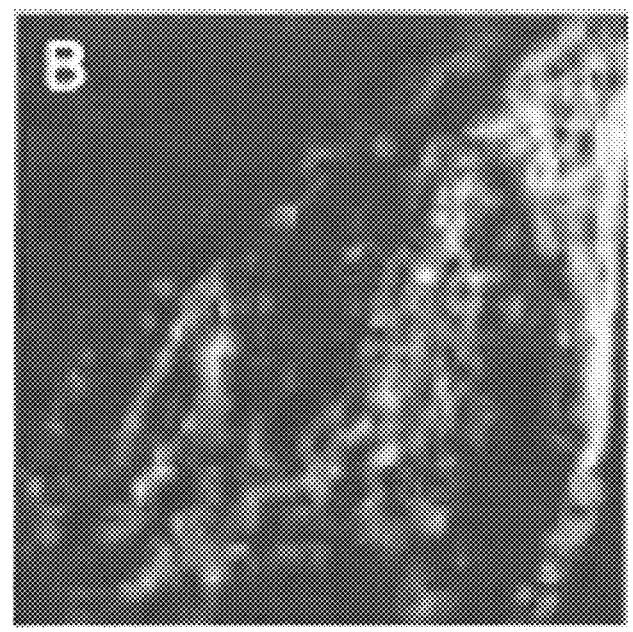
FIG. 6(B) shows images of histochemistry immunofluorescence of cells from the subventricular zone treated with stem cells and mannitol. Cells were stained with DCX and imaged at 20×.
Figure 6C:
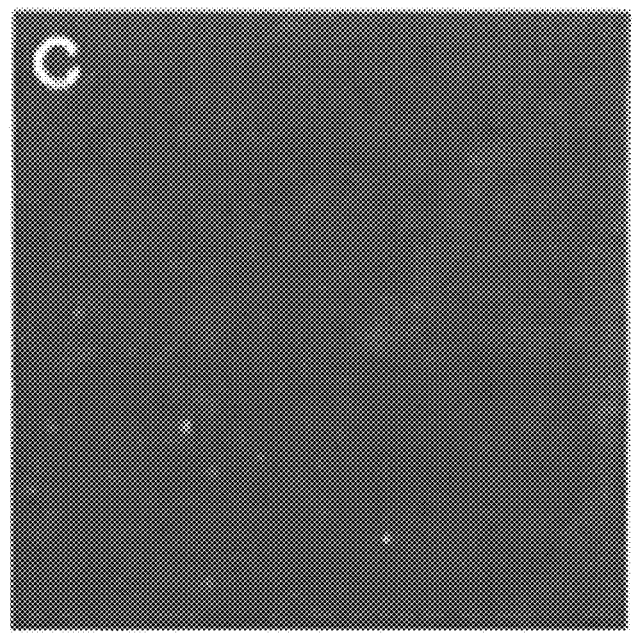
FIG. 6(C) shows images of histochemistry immunofluorescence of cells from the subventricular zone treated with stem cells and mannitol. Cells were stained with HuNu and imaged at 20×.
Figure 6D:
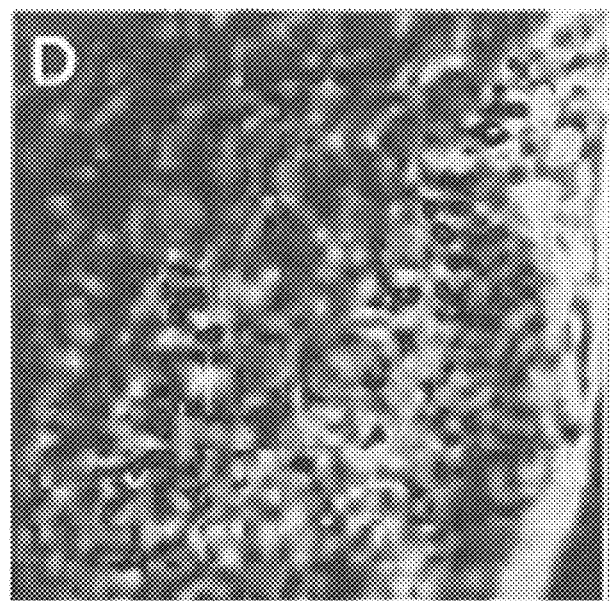
FIG. 6(D) shows images of histochemistry immunofluorescence of cells from the subventricular zone treated with stem cells and mannitol. Cells were stained with DAPI, DCX, and HuNu, and merged images collected at 20×.
Figure 6E:
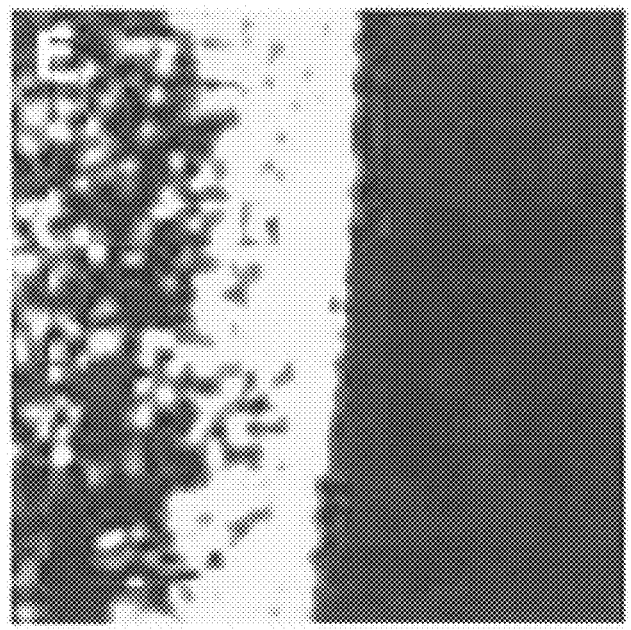
FIG. 6(E) shows images of histochemistry immunofluorescence of cells from the subventricular zone treated with stem cells and mannitol. Cells were stained with DAPI and imaged at 40×.
Figure 6F:
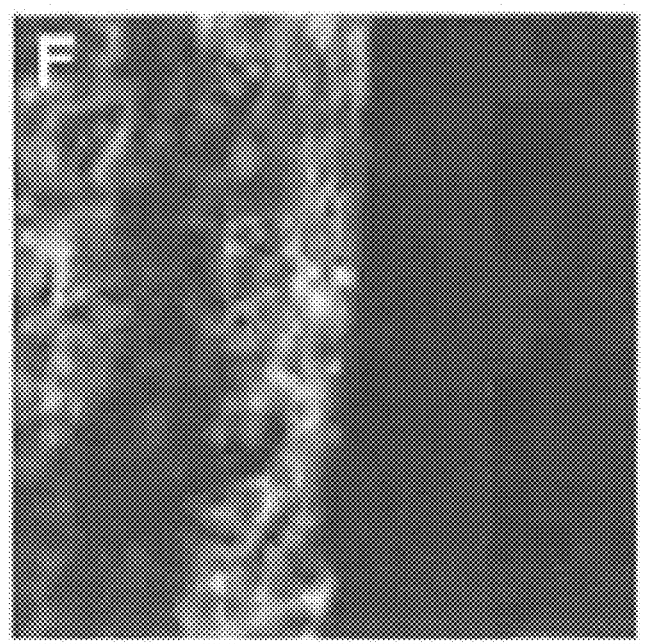
FIG. 6(F) shows images of histochemistry immunofluorescence of cells from the subventricular zone treated with stem cells and mannitol. Cells were stained with DCX and imaged at 40×.
Figure 6G:
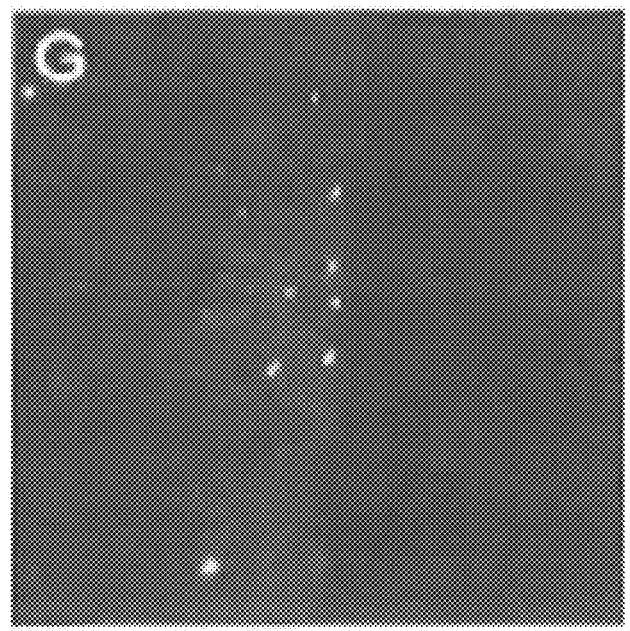
FIG. 6(G) shows images of histochemistry immunofluorescence of cells from the subventricular zone treated with stem cells and mannitol. Cells were stained with HuNu and imaged at 40×.
Figure 6H:
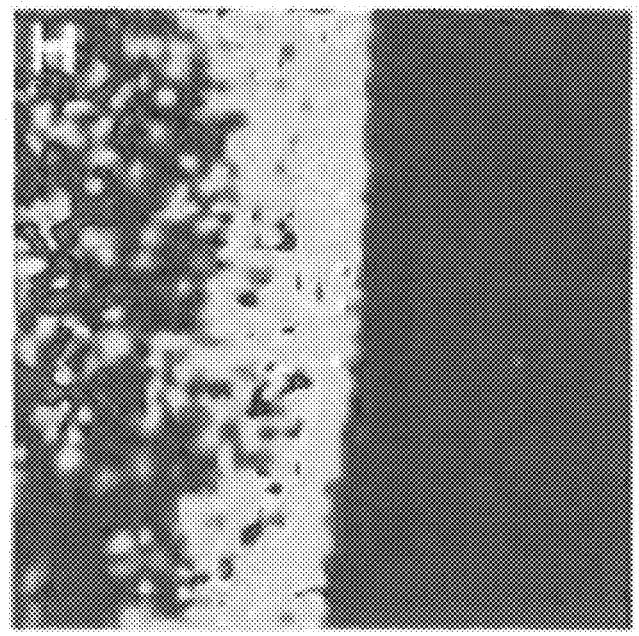
FIG. 6(H) shows images of histochemistry immunofluorescence of cells from the subventricular zone treated with stem cells and mannitol. Cells were stained with DAPI, DCX, and HuNu, and merged images collected at 40×.

Staining of the cerebral cortex showed that while hUCBC treatment reduced neuronal death, as seen in FIG. 3(A), treatment with hUCBC and BBB (mannitol) greatly enhanced survival, as seen in FIG. 4(A). Staining for doublecortin (DCX), a microtubule protein found in neuron precursors and immature neurons, showed hUCBC stimulated neurogenesis, seen in FIG. 3(B), though inclusion of BBB with the hUCBC treatment significantly increased neurogenesis, as seen in FIG. 4(B). HuNu staining illustrated a similar pattern, as seen in FIGS. 3(C) and 4(C). Merging of the staining indicated that new neuronal progenitor cells migrated from the periphery to the stroke site, seen in FIGS. 3(D) and 4(D). Staining of the subventricular zone (SVZ) similarly shows hUCBC limits neuronal death, as seen in FIGS. 5(A) and (E), though considerably less so than hUCBC and BBB treatment, as seen in FIGS. 6(A) and (E). However, doublecortin was limited to the periphery of the SVZ in hUCBC-only treated rats, as seen in FIGS. 5(B) and (F), whereas doublecortin staining was more widely seen in the SVZ of rats treated with hUCBC and BBB, as seen in FIGS. 6(B) and (F). Neuronal precursor staining showed little signal in hUCBC-treated rats, seen in FIGS. 5(C) and (G). By comparison, HuNu staining was seen in hUCBC and BBB-treated rats, albeit at low levels, as seen in FIGS. 6(C) and (G). The neuronal survival appears to correlate with influx of neuron precursors, as seen in FIGS. 5(D), (H), 6(D), and (H). The use of BBB in permeation in chronic stroke facilitates migration of stem cells from the periphery to the stroke site, and BBB permeation lowers the number of stem cells needed to effectively cause functional improvement in stroke.

Figure 7:
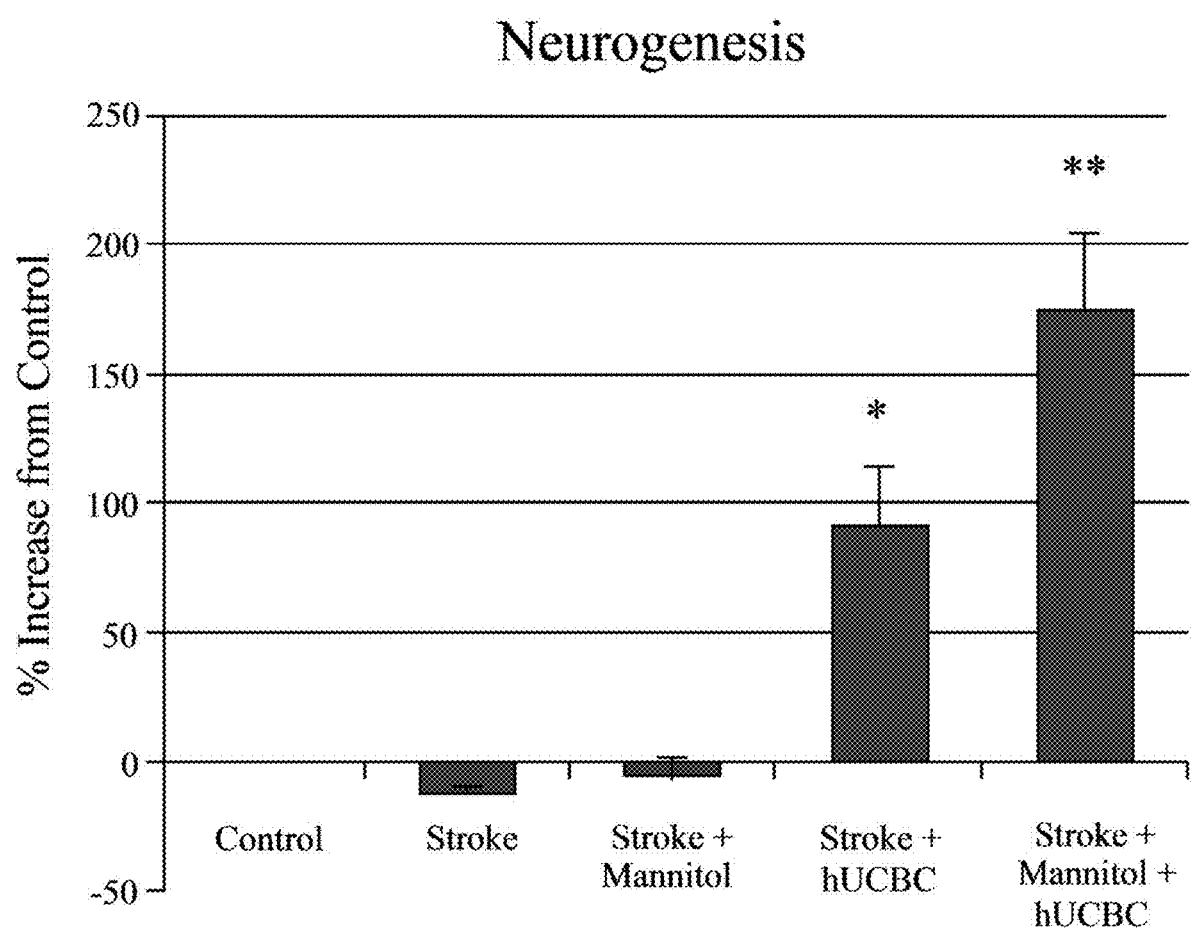
FIG. 7 is a graph showing mannitol's effect on neurogenesis. *$p>0.05$ significantly increased neurogenesis vs. control, stroke (vehicle only), stroke with mannitol. **$p>0.05$ significantly increased neurogenesis vs. all groups.

Analysis indicates that rats subjected to MCAO, or rats subjected to MCAO and treated with BBB were subjected to neuronal death without concomitant neurogenesis, as seen in FIG. 7. By comparison, adding hUCBC to MCAO-afflicted rats increased neurogenesis significantly, about 100% above sham-operated rats. Furthermore, adding hUCBC with BBB significantly increased neurogenesis more, to around 175% that of sham control.

Results revealed that vehicle- and mannitol-treated stroke rats displayed significant deficits in behavioral (motor abnormalities) and histological (brain damage) parameters compared to sham surgery animals (control) (p's<0.05). In contrast, while stroke animals that received human umbilical cord stem cells alone or combined human umbilical cord stem cells and mannitol also displayed significant behavioral and histological deficits compared to control animals (p's<0.05), these transplanted stroke animals exhibited significantly improved motor performance and significantly better brain cell survival in the peri-infarct area compared to stroke animals that received vehicle or mannitol alone (p's<0.05).

Moreover, BBB permeation in chronic stroke was found to lower the effective stem cell dose necessary to improve functional outcome. Of note, the significant improvement in motor performance and significant increase in brain cell survival in the peri-infarct area were comparable between stroke animals that received human umbilical cord stem cells alone and combined human umbilical cord stem cells and mannitol (p's >0.05). Finally, BBB permeation in chronic stroke enhanced neurogenesis as revealed by increased number of newborn cells in the stroke brain in those animals treated with combined human umbilical cord stem cells and mannitol compared to all other treatment groups (p's<0.05). In summary, BBB permeation in chronic stroke facilitated the migration of stem cells from the periphery to the stroke, and that BBB permeation lowered the number of stem cells needed to effectively cause functional improvement in stroke, likely via a therapeutic mechanism involving the enhancement of neurogenesis.

As seen above, BBB permeation in the chronic stage of stroke assisted in the entry of stem cells from the periphery to the stroke brain, which improves therapeutic efficacy of hUCBC and allows for lower doses of hUCBC in treatment of stroke.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of increasing neurogenesis in a patient having a chronic stroke comprising the steps:
   identifying a patient suffering from chronic stroke wherein an initial stroke insult occurred at least one month prior;
   obtaining umbilical cord blood stem cells; and
   administering a therapeutically effective amount of the umbilical cord blood stem cells and a blood brain barrier permeabilizer to the patient after the acute and subacute phases of the stroke insult wherein the blood brain permeabilizer is selected from the group consisting of mannitol and lobradimil wherein the therapeutically effective amount of the umbilical cord blood stem cells is administered at one month post-stroke;
   wherein administration of the therapeutically effective amount of the umbilical cord blood stem cells and the blood brain permeabilizer facilitates migration of the umbilical cord blood stem cells from periphery to stroke site and increases neurogenesis in the patient.

2. The method of claim 1, wherein the umbilical cord blood stem cells and the blood brain permeabilizer are administered concomitantly to the patient.

3. The method of claim 1, wherein the umbilical cord blood stem cells and the blood brain permeabilizer are administered intra-arterially.

4. The method of claim 3, wherein infusion rate of the umbilical cord blood stem cells and the blood brain permeabilizer is 1 µl per minute.

5. The method of claim 1, wherein the umbilical cord blood stem cells are mononucleated cells.

6. The method of claim 1, wherein the umbilical cord blood stem cells are administered separately from the blood brain permeabilizer with a temporal separation between the administration of the umbilical cord blood stem cells and the blood brain permeabilizer.

7. The method of claim 6, wherein the temporal separation is less than a minute.

8. The method of claim 6, wherein the temporal separation is at least one hour.

9. The method of claim 1, wherein neurogenesis is increased about 175% as compared to a sham control.

* * * * *